(12) United States Patent
Ying et al.

(10) Patent No.: US 8,933,276 B2
(45) Date of Patent: Jan. 13, 2015

(54) HETEROGENEOUS CHIRAL CATALYST

(75) Inventors: Jackie Y. Ying, Singapore (SG); Yugen Zhang, Singapore (SG); Su Seong Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 644 days.

(21) Appl. No.: 12/161,547

(22) PCT Filed: Jan. 19, 2006

(86) PCT No.: PCT/SG2006/000009
§ 371 (c)(1),
(2), (4) Date: Oct. 23, 2008

(87) PCT Pub. No.: WO2007/084075
PCT Pub. Date: Jul. 26, 2007

(65) Prior Publication Data
US 2009/0281358 A1   Nov. 12, 2009

(51) Int. Cl.
C07C 45/56 (2006.01)
B01J 31/02 (2006.01)
C07C 45/69 (2006.01)
C07D 207/333 (2006.01)
C07D 233/32 (2006.01)
C07F 7/18 (2006.01)
C07F 7/08 (2006.01)

(52) U.S. Cl.
CPC ............. *C07C 45/69* (2013.01); *B01J 31/0295* (2013.01); *B01J 2231/4205* (2013.01); *C07D 207/333* (2013.01); *C07D 233/32* (2013.01); *C07F 7/1844* (2013.01); *C07F 7/0812* (2013.01); *B01J 2231/326* (2013.01); *C07B 2200/11* (2013.01)
USPC .......................................... 568/458; 502/158

(58) Field of Classification Search
None
See application file for complete search history.

(56) References Cited

U.S. PATENT DOCUMENTS

2009/0170692 A1*  7/2009  Ying et al. .................... 502/155
2010/0105544 A1*  4/2010  Ying et al. .................... 502/152
2011/0034700 A1   2/2011  Ying et al.

FOREIGN PATENT DOCUMENTS

JP   2008-532745 A    8/2008
WO   WO 01/53269 A1    7/2001
WO   WO 03/047740 A2   6/2003
WO   WO 2006/096131 A1 9/2006

OTHER PUBLICATIONS

Park et al. Tetrahedron:Asymmetry 12(2001)2931-2935.*
Dumitriu et al., Journal of Molecular Catalysis B: Enzymatic 22 (2003) 119-133.*
Ahrendt, K.A., et al., "New strategies for organic catalysts: The first highly enantioselective organocatalytic Diels-Alder reaction," 2000, *J. Am. Chem. Soc.*, vol. 122, pp. 4243-4244.
Benaglia, M., et al., "Poly(ethylene glycol)-supported chiral imidazolidin-4-one: An efficient organic catalyst for the enantioselective Diels-Alder cycloaddition," 2002, *Adv. Synth. Catal.*, vol. 344, No. 2, pp. 149-152.
Benaglia, M., et al., "Polymer-supported organic catalysts," 2003, *Chem. Rev.*, vol. 103, No. 9, pp. 3401-3429.
Lancaster, T.M., et al., "Effect of surface modification on the reactivity of MCF-supported IndaBOX," 2005, *Chem. Commun.*, pp. 3577-3579.
Lancaster, Thomas M. (2004) *Silica mesocellular foam and carbon nanofoam for fine chemical synthesis and separation*. Ph.D. thesis. Massachusetts Institute of Technology, Department of Chemical Engineering. [Abstract only] http://hdl.handle.net/1721.1/29373.
Paras, N.A. and W.C. MacMillan, "New strategies in organic catalysts: The first enantioselective organocatalytic Friedel-Crafts alkylation," 2001, *J. Am. Chem. Soc.*, vol. 123, pp. 4370-4371.
Puglisi, A., et al., "Enantioselective 1,3-dipolar cycloadditions of unsaturated aldehydes promoted by a poly(ethylene glycol)-supported organic catalyst," 2004, *Eur. J. Org. Chem.*, pp. 567-573.
Schmidt-Winkel, P., et al., "Mesocellular siliceous foams with uniformly sized cells and windows," 1999, *J. Am. Chem. Soc.*, vol. 121, pp. 254-255.
Selkälä, S.A., et al., "Asymmetric organocatalytic Diels-Alder reactions on solid support," 2002, *Adv. Synth. Catal.*, vol. 344, No. 9, pp. 941-945.
Zhao, D., et al., "Triblock copolymer syntheses of mesoporous silica with periodic 50 to 300 angstrom pores," 1998, *Science*, vol. 279, pp. 548-552.

* cited by examiner

*Primary Examiner* — Yun Qian
(74) *Attorney, Agent, or Firm* — Kilpatrick Townsend & Stockton LLP (57) ABSTRACT

The invention provides a heterogeneous catalyst comprising a catalytic group coupled to a mesocellular siliceous foam support. The catalytic group is capable of catalysing a reaction selected from the group consisting of a Friedel-Craft reaction and a Diels-Alder reaction.

18 Claims, 4 Drawing Sheets

HETEROGENEOUS CHIRAL CATALYST

CROSS-REFERENCE TO RELATED PATENT APPLICATIONS

The present patent application claims benefit of priority under 35 U.S.C. §371 as the U.S. National Stage entry of International Application No. PCT/SG2006/000009, International Filing Date Jan. 19, 2006, the disclosure of which is herein incorporated by reference in its entirety.

TECHNICAL FIELD

The present invention relates to heterogeneous catalysts, to processes for making them and to methods for using them.

BACKGROUND OF THE INVENTION

In recent years, there has been a great increase in research activities relating to organic catalysis, especially chiral organic catalysis. Certain simple organic molecules (organocatalysts) are capable of effectively catalyzing a variety of fundamentally important transformations, leading to highly enantioselective products. Unlike organometallic catalysts, organocatalysts do not involve metals, giving them greater applicability in pharmaceuticals industry. However, organocatalysts still have some disadvantages, such as the requirement for high catalyst loading, and the difficulty in catalyst separation from the product stream. Solid supported catalysts have the potential to offer a solution to these disadvantages.

Polymer- or silica-supported imidazolidin-4-one catalysts have been reported before. However, there are no previous reports of imidazolidin-4-ones supported on mesocellular siliceous foam (MCF), and no previous reports of asymmetric Friedel-Crafts alkylation catalyzed by heterogenized catalysts.

A recyclable organocatalyst of high efficiency and enantioselectivity (for example imidazolidin-4-one) supported on MCF, for Friedel-Crafts alkylation and Diels-Alder cycloaddition, would be desirable. MCF is a novel mesoporous material with unique advantages as a solid support for catalysts. Compared to polymers, this silica support does not have swelling problems, and is more thermally robust. Also, the surface of silica may be easily modified to manipulate the microenvironment of the supported catalyst. Templated by oil-in-water microemulsions, MCF has a high surface area of commonly 500-800 $m^2/g$, and a 3-dimensional pore structure with ultralarge cell-like pores (commonly 23-42 nm) that are connected by windows (commonly 9-22 nm). Such a pore structure may prevent steric issues associated with the immobilization of bulky compounds, and may minimize any diffusion limitation of large substrates.

Imidazolidin-4-one 1 (FIG. 1) is a chiral organocatalyst which has been used as an efficient catalyst for a variety of highly enantioselective reactions. It also has great application potential in industry. Therefore, heterogenization of this organocatalyst would be very attractive. Imidazolidin-4-one supported on polymer and silica gel was recently studied for cycloaddition reactions. However, the reported chemical efficiency of these heterogenized catalysts was much lower than the homogeneous catalyst.

It would therefore be desirable to produce a heterogeneous catalyst of comparable chemical and stereochemical efficiency to unsupported imidazolidin-4-one.

OBJECT OF THE INVENTION

It is an object of the present invention to overcome or substantially ameliorate at least one of the above disadvantages.

SUMMARY OF THE INVENTION

In a first aspect of the invention there is provided a heterogeneous catalyst comprising a catalytic group coupled to a mesocellular siliceous foam support, wherein the catalytic group is capable of catalysing a reaction selected from the group consisting of a Friedel-Craft reaction and a Diels-Alder reaction. The catalytic group may be capable of catalysing a Friedel-Craft reaction and of catalysing a Diels-Alder reaction. The catalyst may be capable of catalysing the reaction.

The catalytic group, and the catalyst, may be capable of catalysing the reaction with high enantioselectivity. The catalytic group may be chiral, and may have greater than about 70, 75, 80, 85, 90 or 95% (+) chirality or greater than about 70, 75, 80, 85, 90 or 95% (−) chirality. They may be capable of catalysing the reaction to produce a chiral product. The catalytic group may comprise an imidazolidin-4-one group. It may comprise a substituted or unsubstituted imidazolidin-4-one group. The catalyst may be a heterogeneous catalyst. It may be a chiral catalyst. It may be a catalyst for Friedel-Craft reaction (e.g. alkylation) and/or for Diels-Alder reaction. It may be capable of catalysing reaction of reagents to produce a chiral, or asymmetric, product. It may be capable of catalysing a reaction to produce a product with an enantiomeric excess (ee) of greater than about 50%, or greater than about 60, 70, 80 or 90%. It may be capable of catalysing a reaction to produce a product with a yield of at least about 20%, or at least about 50, 70 or 90%. It may be capable of catalysing a Diels-Alder reaction wherein the product of the reaction has an exo/endo ratio that is not 1. The exo/endo ratio may be at least about 1.2 to 1, or may be 1 to at least about 1.1. The catalyst may be reusable and/or recyclable. It may be reused or recycled at least 1, 2, 3, 4 or 5 times or more than 5 times. It may be removable from a reaction mixture, e.g. by filtration, centrifugation, ultracentrifugation or settling.

The catalyst may be a solid catalyst, and may be a particulate catalyst. The support may be a particulate support, and may be a particulate foam. It may have a particle size between about 1 and about 50 microns, or between about 2 and about 20 microns. The support may have a 3-dimensional structure comprising pores connected by windows. The windows may be smaller than the pores. The pores may be between about 20 and 50 nm in diameter. The windows may be between about 5 and 20 nm in diameter. The support may comprise silica, and may also comprise some other metal oxide, for example alumina, titania or zirconia. The support may have a BET surface area of between about 400 and about 1000 $m^2/g$, or between about 500 and about 800 $m^2/g$. The support may have hydrophobic groups coupled thereto. The hydrophobic groups may be on at least a portion of the surface of the support. In this context, the surface comprises the outer surface, the surface of the pores and the surface of the windows of the support. The hydrophobic groups may be alkylsilyl groups, for example mono-, di- or tri-alkylsilyl groups. They may be for example trimethylsilyl groups. The support may have one or more chiral modifiers coupled thereto. The chiral modifier(s) may be different to the catalytic species. The chiral modifier may for example comprise an amine bearing a chiral group, or may comprise some other asymmetric or chiral group.

The catalytic group may be coupled to the support by a linker group. The linker group may comprise an attachment group for attaching the linker group to the support, and may comprise a spacer group for coupling the attachment group to the catalytic group. The linker group may be a silyl group, for example a dialkylsilyl (e.g. dimethylsilyl) group. The spacer group may comprise one or more of an alkyl group, an aryl group, a heteroaryl group and a heteroatom, and may comprise more than one of any one or more of these. It may for example comprise —(CH$_2$)$_4$—O—C$_6$H$_4$—CH$_2$— or —(CH$_2$)$_2$—O—(CH$_2$)$_4$—. The chiral modifier, if present, may be coupled to the support by a linker group, which may be as described above. The linker group for the chiral modifier may be the same as or different to the linker group for the catalytic group.

The catalytic group may comprise an imidazolidin-4-one group. The imidazolidin-4-one group may be chiral. It may be at least 75%, at least 80% or at least 90% (+) isomer, or may be at least 75%, at least 80% or at least 90% (−) isomer. It may be chiral due to asymmetry of the carbon atom adjacent to the carbonyl group. It may have asymmetry in one or more of a group linked to or attached to the ring carbon atom (C5) adjacent to the carbonyl group, the ring carbon atom (C2) between the two nitrogen atoms and a group linked to or attached to the ring carbon atom (C2) between the two nitrogen atoms. It may be coupled to the support through the ring nitrogen (N3) adjacent to the carbonyl group or through the ring carbon (C5) adjacent to the carbonyl group. The imidazolidin-4-one group may be substituted in the 5 position (i.e. on C5) by an arylmethyl group, e.g. R—C$_6$H$_4$—CH$_2$—, wherein R may be H, or a functional substituent, or an alkyl or aryl substituent or some other substituent, and/or may comprise a linker group or portion thereof or an attachment group for coupling the imidazolidin-4-one group to the support. The aryl group may be ortho-, meta- or para-substituted.

In an embodiment there is provided a catalyst comprising a chiral imidazolidin-4-one group coupled to a mesocellular siliceous foam support.

In another embodiment there is provided a catalyst comprising a chiral imidazolidin-4-one group coupled to a mesocellular siliceous foam support, wherein the support has hydrophobic groups on the surface thereof and/or on the surface of the pores and/or windows thereof.

In another embodiment there is provided a catalyst comprising a chiral is imidazolidin-4-one group coupled to a mesocellular siliceous foam support, wherein the support has one or more chiral modifiers coupled thereto.

In another embodiment there is provided a heterogeneous catalyst comprising a 5-(phenylmethyl)imidazolidin-4-one group coupled through N3 to a mesocellular siliceous foam support by —(CH$_2$)$_2$—O—(CH$_2$)$_4$—Si(Me$_2$)-, and also comprising trimethylsilyl groups coupled to the support.

In another embodiment there is provided a heterogeneous catalyst comprising a 3-alkylimidazolidin-4-one group coupled through C5 to a mesocellular siliceous foam support by —CH$_2$—C$_6$H$_4$—O—(CH$_2$)$_4$—Si(Me$_2$)-, and also comprising trimethylsilyl groups coupled to the support.

In a second aspect of the invention there is provided a process for making a heterogeneous catalyst comprising coupling a catalytic group to a mesocellular siliceous foam support, wherein the catalytic group is capable of catalysing a reaction selected from the group consisting of a Friedel-Craft reaction and a Diels-Alder reaction.

The process may comprise reacting the mesocellular siliceous foam support with a reagent which comprises the catalytic group, said reagent being capable of reacting with the support. The reagent may be capable of reacting with OH groups, for example silanol groups, on the support. The reagent may comprise a reactive group, for example a reactive silicon group, capable of reacting with the OH, e.g. coupling with, groups on the support. It may be capable of reacting with the OH groups to form a siloxane (Si—O—Si) linkage. The reactive group may be for example a dimethylsilylallyl (or allyl dimethylsilyl) group. The reaction of the dimethylsilylallyl group with the support may be acid catalysed. The reagent may comprise a spacer group which couples the reactive group to the catalytic group. The reactive group may be such that, on reacting with the OH groups on the support, it is converted to an attachment group, as described in the first aspect of the invention.

The process may also comprise the step of at least partially hydrophobing the mesocellular siliceous foam support. The step of at least partially hydrophobing may comprise reacting the support with a hydrophobing agent, for example an alkylsilicon species such as hexamethyldisiloxane, hexamethyldisilazane or trimethylsilyl chloride or some other suitable hydrophobing agent. The step of at least partially hydrophobing may be conducted before or after or at the same time as reacting the support with the reagent which comprises the catalytic group.

The process may comprise the step of reacting the mesocellular siliceous foam support with a chiral modifying reagent in order to couple a chiral modifier to the support, said chiral modifying reagent comprising the chiral modifier. This step may be conducted before, after or during one or both of the steps of reacting the mesocellular siliceous foam support with the reagent which comprises the catalytic group and at least partially hydrophobing the support (if the latter step is conducted). That is, the three steps may be conducted in any desired order, or any two or more of the steps may be conducted concurrently. The chiral modifying reagent may comprise the chiral modifier described in the first aspect of the reaction. The chiral modifying reagent may be capable of reacting with OH groups, for example silanol groups, on the support. The chiral modifying reagent may comprise a reactive group, for example a reactive silicon group, capable of reacting with the OH groups on the support. The reactive group may be the same as that in the reagent which comprises the catalytic group, or it may be a different reactive group. The chiral modifying reagent may comprise a spacer group which couples the reactive group to the catalytic group. The spacer group may be the same as that in the reagent which comprises the catalytic group or it may be a different spacer. It may satisfy the same requirements as described above for the spacer of the reagent which comprises the catalytic group. The reactive group of the chiral modifying reagent may be such that, on reacting with the OH groups on the support, it is converted to an attachment group, as described in the first aspect of the invention.

The process may additionally comprise the step of preparing the reagent which comprises the catalytic group. This step may comprise coupling the reactive group, or a precursor thereto, to the catalytic group or a precursor thereto. It may comprise converting a chiral amino acid, or derivative thereof, into the reagent, said reagent comprising a chiral imidazolidin-4-one group. The derivative may be a salt (e.g. an N-terminal ammonium salt), for example a hydrochloride salt. The derivative may be an ester (e.g. a C-terminal ester) for example an alkyl ester such as a methyl, ethyl, propyl, isopropyl, butyl, isobutyl or tertiary butyl ester.

In an embodiment there is provided a process for making a heterogeneous catalyst comprising:
preparing a reagent comprising a catalytic group, said catalytic group being capable of catalysing a reaction selected from the group consisting of a Friedel-Craft reaction and a Diels-Alder reaction, and said reagent being capable of reacting with OH groups on mesocellular siliceous foam; and reacting the reagent with a mesocellular siliceous foam support to make the heterogeneous catalyst.

In another embodiment there is provided a process for making a heterogeneous catalyst comprising:

reacting a reagent with a mesocellular siliceous foam support to make a heterogeneous catalyst; and at least partially hydrophobing the mesocellular siliceous foam support.

wherein the reagent comprises a catalytic group, said catalytic group being capable of catalysing a reaction selected from the group consisting of a Friedel-Craft reaction and a Diels-Alder reaction, and wherein said reagent is capable of reacting with OH groups on the mesocellular siliceous foam.

In another embodiment there is provided a process for making a heterogeneous catalyst comprising:

at least partially hydrophobing a mesocellular siliceous foam support; and reacting a reagent with the mesocellular siliceous foam support to make the heterogeneous catalyst;

wherein the reagent comprises a catalytic group, said catalytic group being capable of catalysing a reaction selected from the group consisting of a Friedel-Craft reaction and a Diels-Alder reaction, and wherein said reagent is capable of reacting with OH groups on the mesocellular siliceous foam.

In another embodiment there is provided a process for making a heterogeneous catalyst comprising:

reacting a chiral modifying reagent with a mesocellular siliceous foam support in order to couple a chiral modifier to the support, said chiral modifying reagent comprising the chiral modifier; and reacting a reagent with the mesocellular siliceous foam support to make the heterogeneous catalyst;

wherein the reagent comprises a catalytic group, said catalytic group being capable of catalysing a reaction selected from the group consisting of a Friedel-Craft reaction and a Diels-Alder reaction, and wherein said reagent is capable of reacting with OH groups on the mesocellular siliceous foam.

In another embodiment there is provided a process for making a heterogeneous catalyst comprising coupling a chiral imidazolidin-4-one group to a mesocellular siliceous foam support.

In another embodiment there is provided a process for making a heterogeneous catalyst comprising reacting a mesocellular siliceous foam support with a reagent which comprises a chiral imidazolidin-4-one group, said reagent being capable of reacting with the support.

In another embodiment there is provided a process for making a heterogeneous catalyst comprising:

at least partially hydrophobing a mesocellular siliceous foam support; and reacting the mesocellular siliceous foam support with a reagent which comprises a chiral imidazolidin-4-one group, said reagent being capable of reacting with the support.

In another embodiment there is provided a process for making a heterogeneous catalyst comprising:

reacting a chiral modifying reagent with a mesocellular siliceous foam support in order to couple a chiral modifier to the support, said chiral modifying reagent comprising the chiral modifier; and reacting a reagent with the mesocellular siliceous foam support to make a heterogeneous catalyst, wherein said reagent comprises a chiral imidazolidin-4-one group, and wherein said reagent is capable of reacting with OH groups on the mesocellular siliceous foam.

In another embodiment there is provided a process for making a heterogeneous catalyst comprising the steps of:

a) reacting a salt of a tyrosine ester with an alkyl amine and acetone to produce a 3-alkyl-2,2-dimethyl-5-(4-hydroxyphenylmethyl)imidazolidin-4-one;

b) reacting the 3-alkyl-2,2-dimethyl-5-(4-hydroxyphenylmethyl)imidazolidin-4-one with an allyl dimethyl haloalkylsilane to produce a chiral reagent comprising a 2,2,3-trisubstituted imidazolidin-4-one-5-yl group;

c) coupling the chiral reagent with mesocellular siliceous foam at elevated temperature in the presence of an acid catalyst; and d) reacting the mesocellular siliceous foam with a trimethylsilylating agent.

Step d) may be conducted before, during or after step c).

In another embodiment there is provided a process for making a heterogeneous catalyst comprising the steps of:

a) reacting a salt of a phenylalanine ester with a hydroxyalkyl amine and acetone to produce a 3-hydroxyalkyl-2,2-dimethyl-5-(phenylmethyl)imidazolidin-4-one;

b) reacting the 3-hydroxyalkyl-2,2-dimethyl-5-(phenylmethyl)imidazolidin-4-one with an allyl dimethyl haloalkylsilane to produce a chiral reagent comprising a 2,2,5-trisubstituted imidazolidin-4-one-3-yl group;

c) coupling the chiral reagent with mesocellular siliceous foam at elevated temperature in the presence of an acid catalyst; and d) reacting the mesocellular siliceous foam with a trimethylsilylating agent;

Step d) may be conducted before, during or after step c).

The present invention also provides a heterogeneous catalyst when made by the process of the second aspect.

In a third aspect of the invention there is provided a method for producing a product comprising exposing at least one starting material to a heterogeneous catalyst according to the invention, said at least one starting material being capable of undergoing either a Diels-Alder reaction or a Friedel-Craft reaction to produce the product. The method may also comprise allowing the at least one starting material to produce the product. It may comprise allowing the at least one starting material to undergo the reaction (either a Diels-Alder reaction or a Friedel-Craft reaction) to Produce the product.

The product may be a chiral, or asymmetric, product. The catalyst may be a chiral heterogeneous catalyst. The at least one starting material may be two starting materials. The two starting material may be for example a diene and a dienophile capable of undergoing a Diels-Alder reaction together, or may be a Friedel-Craft substrate and a Friedel-Craft reagent, wherein the Friedel-Craft reagent is capable of reacting with, e.g. adding onto, the Friedel-Craft substrate. Alternatively the at least one starting material may be a single starting material comprising a diene portion and a dienophile portion, wherein the single starting material is capable of undergoing an intramolecular Diels-Alder reaction, or may be a single starting material comprising an aromatic Friedel-Craft substrate portion and a Friedel-Craft reagent portion, wherein the single starting material is capable of undergoing an intramolecular Friedel-Craft reaction. The Friedel-Craft substrate and the Friedel-Craft substrate portion may each comprise an aromatic or heteroaromatic nucleus. The Friedel-Craft reaction may be an alkylation or an acylation. The Friedel-Craft reagent and the Friedel-Craft reagent portion may each comprise an alkyl or an acyl group, each of which may be either substituted or unsubstituted. In the case where two starting materials are used, they may be in a molar ratio of between about 3:1 and about 1:3, for example about 3:1, 2:1, 1:1, 1:2 or 1:3.

The method may comprise preparing a heterogeneous reaction mixture. The heterogeneous reaction mixture may be prepared by combining a solution comprising the at least one starting material and the heterogeneous catalyst, or by combining a solvent and the heterogeneous catalyst and then adding the at least one starting material, or by combining a solution of a first starting material and the heterogeneous catalyst and then adding a second starting material. The second starting material may be added in a single portion, or may be added slowly or portionwise over time. The method may additionally comprise agitating the heterogeneous reaction mixture, for example stirring, swirling, shaking or mixing the heterogeneous reaction mixture. Alternatively the at least one starting material and the heterogeneous catalyst may be combined in the absence of a solvent, providing that the at least one starting material is a liquid or a gas or a vapour.

The at least one starting material maybe exposed to the chiral heterogeneous temperature for sufficient time for conversion of at least 80% of at least one of the at least one starting material to the product (i.e. conversion of at least 80% of the starting material in the case of a single starting material, or of at least 80% of at least one of the starting materials in the case of more than one starting material).

The method may comprise exposing at least one starting material to the chiral heterogeneous catalyst at any convenient temperature. The temperature may be below the decomposition temperature of the catalyst, the at least one starting material and the product. The temperature may be such that the reaction mixture is not solid, and may below or equal to the boiling point of the reaction mixture at the pressure at which the method is conducted.

The method may comprise the step of separating the heterogeneous catalyst from the heterogeneous reaction mixture after allowing the at least one starting material to produce the product, to form a catalyst portion and a liquid portion. The separating may comprise filtering, microfiltering, centrifuging, ultracentrifuging, decanting or distilling, or a combination of any two or more of these. The catalyst portion may be washed with a washing solvent, and may be washed a plurality of times with a plurality of washing solvents. The washing solvent(s) may be combined with the liquid portion. The method may comprise isolating the product from the liquid portion. The isolating may comprise any of the known methods for doing so, including any one or more of evaporation, distillation, fractional distillation, preparative gas chromatography, liquid chromatography, preparative high pressure liquid chromatography, preparative thin layer chromatography, crystallisation, recrystallisation, sublimation etc.

The catalyst portion, or a part thereof, may be used as a heterogeneous chiral catalyst in a subsequent reaction, optionally after washing and/or drying.

In an embodiment there is provided a method for producing a product of a Friedel-Craft reaction comprising the steps of:
  a) combining a heterogeneous catalyst according to the invention with a solvent and an acid to form a catalyst mixture;
  b) adding an aromatic compound to the catalyst mixture, said aromatic compound being capable of undergoing a Friedel-Craft reaction;
  c) adding a Friedel-Craft reagent to the catalyst mixture and aromatic compound to form a reaction mixture;
  d) allowing sufficient time for reaction of the aromatic compound with the Friedel-Craft reagent in the reaction mixture; and
  e) isolating the product from a liquid portion of the reaction mixture, said product being a reaction product of the aromatic compound and the Friedel-Craft reagent.

The mole ratio of the aromatic compound to the Friedel-Craft reagent in the reaction mixture may be about 1:2. The aromatic compound may comprise a benzene ring or a fused benzene ring, or may be a heteroaromatic compound, optionally comprising a fused heteroaromatic ring.

In another embodiment there is provided there is provided a method for producing a product of a Diels Alder reaction comprising the steps of:
  a) combining a heterogeneous catalyst according to the invention with a solvent and an acid to form a catalyst mixture;
  b) adding a dienophile to the catalyst mixture;
  c) adding a diene to the catalyst mixture and dienophile to form a reaction mixture;
  d) allowing sufficient time for reaction of the dienophile with the diene in the reaction mixture; and
  e) isolating the product from a liquid portion of the reaction mixture, said product being a Diels Alder addition product of the dieneophile and the diene.

The mole ratio of the dienophile to the diene in the reaction mixture may be about 1:1.2.

The present invention also provides a chiral, or asymmetric, product when made by the method of the third aspect of the invention. It also provides the use of a heterogeneous chiral catalyst according to the invention for producing a chiral, or asymmetric, product by the method of the invention. It further provides a heterogeneous catalyst when used for producing a chiral, or asymmetric, product by the method of the invention.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

By using novel siliceous MCF support and unique immobilization and surface modification schemes, heterogenized catalysts of comparable chemical and stereochemical efficiency to unsupported imidazolidin-4-one have been achieved. The present invention invention involves the synthesis of siliceous mesocellular (MCF) supported catalysts, for example supported imidazolidin-4-one asymmetric catalysts. The heterogenized catalyst has been applied successfully in asymmetric Friedel-Crafts to alkylation and Diels-Alder cycloaddition. Previously, polymer- or silica-supported imidazolidin-4-one catalysts have only shown low chemical efficiency. In the present invention, an imidazolidin- 4-one group was immobilized onto MCF to obtain highly active heterogenized organocatalyst. The surface of MCF may be partially pre-capped with trimethylsilyl (TMS) groups to improve the catalyst efficiency.

MCF-supported imidazolidin-4-one was demonstrated to catalyze Friedel-Crafts alkylation and Diels-Alder cycloaddition effectively and enantioselectively. In contrast, previous examples of imidazolidin-4-one supported on polymer or silica gel only catalyzed Diels-Alder cycloaddition with low chemical efficiency.

Similar approach for immobilizing organic compounds onto MCF can be widely applied towards deriving novel heterogenized organocatalysts for the synthesis of a wide variety of fine chemicals and chiral pharmaceuticals. Such novel catalysts offer high activity, selectivity and stability. They may be easily recycled for reuse, and employed in continuous reactions.

MCF-supported imidazolidin-4-one catalysts have been developed by a direct one-step immobilization process. The MCF surface was modified to modulate the microenvironment of the anchored organocatalyst groups. The heterogenized catalysts showed high enantioselectivity and activity in both asymmetric Friedel-Crafts alkylation and Diels-Alder cycloaddition reactions. Compared to polymer and conventional silica gel supports, the siliceous MCF support provides distinct advantages with its open pore structure, ultralarge pore opening and high surface areas. The inventors found that the MCF surface may be partially pre-capped with TMS groups, which, it is hypothesised, operates to attain separate and well-dispersed organocatalyst groups on the support. The support modification and catalyst immobilization schemes described herein could be broadly applied to achieve active, selective and recyclable heterogenized organocatalysts for fine chemicals and chiral pharmaceuticals syntheses.

The present invention provides a heterogeneous catalyst comprising a catalytic group coupled to a mesocellular siliceous foam support. The catalytic group is capable of catalysing a Friedel-Craft reaction (e.g. alkylation or acylation) and/or a Diels-Alder reaction (cycloaddition).

A suitable catalytic group for this catalyst is the imidazolidin-4-one group. For convenience, the ring atoms of this group may be numbered such that N1 is the ring nitrogen atom that is not adjacent to the carbonyl group, C2 is the carbon atom between the two ring nitrogen atoms, N3 is the nitrogen atom adjacent to the carbonyl group, C4 is the carbonyl carbon group and C5 is the carbon atom adjacent to the carbon atom.

The imidazolidin-4-one group for the present catalyst may be substituted on the amide nitrogen atom (N3). The amide nitrogen substituent may be an alkyl group, optionally substituted, for example a methyl, ethyl, propyl, isopropyl, butyl, isobutyl or tertiary butyl group, or may be an aryl or heteroaryl group, optionally substituted, for example a phenyl group. Alternatively, the imidazolidin-4-one group may be coupled through the amide nitrogen N3 to the support. The catalytic group may be chiral. It may comprise at least about 70% of a single stereoisomer (either (+) or (−)), or at least about 75, 80, 85, 90, 95 or 99%, and may comprise about 70, 75, 80, 85, 90, 91, 92, 93, 94, 95, 96, 97, 98, 99, 99.1, 99.2, 99.3, 99.4, 99.5 or more than 99.5% of a single stereoisomer.

The catalytic group may be present in the catalyst at between about 0.05 and about 5 mmol/g, or between about 0.05 and 2, 0.05 and 1, 0.05 and 0.5, 0.05 and 0.1, 0.1 and 5, 0.5 and 5, 1 and 5, 0.1 and 1, 0.5 and 1 or 0.1 and 0.5, and may be present at about 0.05, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5 or 5 mmol/g.

The ring carbon between the two nitrogen atoms (C2) may be substituted, and may be disubstituted. The two groups on that ring carbon may, independently, be hydrogen, an alkyl group, an aryl group or a heteroaryl group as described above. The two groups may be the same or different. The ring carbon between the two nitrogen atoms may have two methyl groups attached thereto.

The ring carbon atom adjacent to the carbonyl group may have either one or two substituents other than hydrogen. The one or two substituents may be disposed such that the carbon atom adjacent the carbonyl group has either (S) or (R) stereochemistry. The substituents on that carbon atom may be, independently, hydrogen, alkyl, aryl or heteroaryl, optionally substituted, as described above, or may be arylalkyl, optionally substituted. The substituents on that carbon atom may be different, so as to provide chirality to the catalytic group. An example of suitable substituents includes hydrogen and phenylmethyl. Alternatively the imidazolidin-4-one group may be coupled through the ring carbon adjacent the carbonyl group to the support.

The catalyst may be capable of catalysing a reaction of reagents to produce a product (e.g. a Diels-Alder or Friedel-Craft product) with enantiomeric excess (ee) of greater than about 50%, or greater than about 60, 70, 80, 90, 91, 92, 93, 94 or 95%. The product may have ee of about 50, 55, 60, 65, 70, 75, 80, 85, 90, 91, 92, 93, 94, 95, 96, 97, 98, 99 or 99.5%. The yield of the product may be greater than about 20% (based on the starting material or based on one of the starting materials), or greater than about 30, 40, 50, 60, 70, 80, 90 or 95%, and may be about 30, 40, 50, 60, 70, 80, 90, 91, 92, 93, 94, 95, 96, 97, 98 or 99%. The yield and/or enantioselectivity and/or the rate of reaction may depend on the reaction conditions, e.g. time, temperature, under which the reaction is run. The ratio of endo to exo in a Diels-Alder product produced using the catalyst of the invention may be between about 5 and about 0.2 (i.e. the amount of endo divided by the amount of exo), or between about 5 and 0.5, 5 and 1, 5 and 2, 2 and 0.2 2, 0.2 and 1, 0.2 and 0.5, 0.5, 1 and 2 or 0.5 and 1, and may be about 0.2, 0.3, 0.4, 0.5, 0.6, 0.7, 0.8, 0.9, 1, 1.5, 2, 2.5, 3, 3.5, 4, 4.5 or 5. It may be greater than 5 or less than 0.2, or greater than 1.2 or less than 0.9.

The catalyst may be reusable and/or recyclable. It may be reused at least 1, 2, 3, 4 or 5 times without substantial loss of product yield or without substantial loss of product ee. Substantial loss in this context may be loss of more than about 30%, or more than about 25, 20, 15, 10 or 5%.

The catalyst, and the support, may be solid. They may be particulate. They may be mesoporous. They may comprise mesoporous particulate foam. The particle size of the catalyst and of the support may be between about 1 and about 50 microns, or between about 1 and 25, 1 and 10, 1 and 5, 5 and 50, 10 and 50, 25 and 50, 2 to 10, 5 and 20 or 20 and 20 microns, and may be about 1, 2, 3, 4, 5, 10, 15, 20, 25, 30, 35, 40, 45 or 50 microns. In this context, particle size refers to the mean particle diameter. The catalyst, and the support, may have a structure comprising relatively large pores connected by relatively small windows. The pores may be between about 20 and 50 nm in diameter, or between about 20 and 40, 20 and 30, 30 and 50, 40 and 50 or 30 and 50 nm in diameter, and may be about 20, 25, 30, 35, 40, 45 or 50 nm in diameter. The windows may be between about 5 and 20 nm in diameter, or between about 5 and 15, 5 and 10, 10 and 20, 15 and 20 or 10 and 15 nm in diameter, and may be about 5, 10, 15 or 20 nm in diameter. The ratio between the pore size and the window size may be about 25:1 and 1.5 to 1, or between about 25:1 and 2:1, 25:1 and 5:1, 15:1 and 10:1, 20:1 and 1.5:1, 10:1 and 1.5:1, 5:1 and 1.5:1, 20:1 and 2:1, 10:1 and 2:1, 10:1 and 5:1, 20:1 and 5:1 or 20:1 and 10:1, and may be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2.5:1, 2:1 or 1.5:1. The BET surface area of the catalyst, or of the support, may be between about 400 and about 100 m$^2$/g, or between about 400 and 800, 400 and 600, 500 and 1000, 700 and 1000, 500 and 800 or 500 and 600 m$^2$/g, and may be about 400, 450, 500, 550, 600, 650, 700, 750, 800, 850, 900, 950 or 1000 m$^2$/g.

The support may have hydrophobic groups on the surface thereof. These hydrophobic groups may be different to the catalytic group. The hydrophobic groups may be alkylsilyl groups, for example di- or tri-alkylsilyl groups. The alkyl group may be a C1 to C6 branched chain or straight chain alkyl group, for example methyl, ethyl, propyl, isopropyl etc. Alternatively the hydrophobic groups may be arylsilyl groups. Suitable hydrophobic groups include trimethylsilyl, dimethylsilylene, triethylsilyl, triphenylsilyl etc. The hydrophobic groups, if present, may be present in the catalyst at between about 0.1 to 2 mmol/g, or between about 0.5 and 2, 1 and 2, 0.1 and 1, 0.1 and 0.5, 0.5 and 1 or 0.7 and 0.9 mmol/g, and may be present at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2 mmol/g.

The support may have one or more chiral modifiers coupled thereto. The chiral modifier may serve to increase the stereoselectivity of the catalyst relative to the same catalyst without the chiral modifier. The chiral modifier may comprise an asymmetric carbon atom. It may for example comprise a urea species wherein at least one of the nitrogen atoms bears a carbon having three different substituents. The three substituents may be selected from hydrogen, alkyl (C1 to C6 straight chain or branched) and substituted alkyl (C1 to C6 straight chain or branched), and may be for example methylol ($CH_2OH$) and/or isopropyl. The chiral modifier may be coupled to the support through a linker group, such as a trimethylene silyl group. The chiral modifier may be present on the support at between about 0.1 to 2 mmol/g, or between about 0.5 and 2, 1 and 2, 0.1 and 1, 0.1 and 0.5, 0.5 and 1 or 0.7 and 0.9 mmol/g, and may be present at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2 mmol/g.

The catalytic group may be coupled to the support by a linker group. If the catalytic group is an imidazolidin-4-one group, the linker group may be attached either to the amide nitrogen atom (N3) or to the ring carbon atom (C5) adjacent the carbonyl group. The linker group may comprise a spacer group attached to the catalytic group, and an attaching group attached to the support. The linker group may be any suitable group capable of providing sufficient distance between the support and the catalytic group to allow efficient catalysis by the catalytic group. The linker group may be at least about 5 atoms in length, or between about 5 and 20 atoms in length, or between about 5 and 10, 10 and 20, 5 and 15, 7 and 12 or 7 and 15 atoms in length, and may be 5, 6, 7, 8, 9, 10, 11 12, 13, 14, 15, 16, 17, 18, 19 or 20 atoms in length. It may comprise an alkyl chain, an aryl group, a heteroatom or more than one of these. Examples include $(CH_2)_2O\ (CH_2)_4$ and $CH_2C_6H_4O\ (CH_2)_4$. The attachment group may be any attachment group capable of connecting the linker group to the support. It may for example comprise a silyl group, e.g. dimethylsilyl.

The heterogeneous catalyst may be made by coupling a catalytic group to a mesocellular siliceous foam support. Thus a reagent comprising the catalytic group may be reacted with the support. The reagent may additionally comprise a linker group as described above and a reactive group capable of reacting with the support, e.g. with silanols on the support. Convenient reactive groups for this purpose include dimethylallylsilyl, whereby the reactive group may react with the silanols by deallylation, optionally acid catalysed deallylation, or dimethylchlorosilyl, whereby the reactive group may react with the silanols by dehydrohalogenation. The inventors have found, surprisingly, that the coupling of dimethylallylsilyl-functional compounds with silanol groups on a substrate by deallylation may be conducted with high efficiency and/or high yield (relative to earlier work) by using an acid catalyst, for example p-toluenesulfonic acid. Earlier work had achieved comparable yields only when acidic surfaces e.g. FSM-16 were used as substrates for the reaction.

The process for making the heterogeneous catalyst may also comprise at least partially hydrophobing the support prior to, or subsequent to, or at the same time as, reaction with the reagent comprising the catalytic group. This may be achieved by any of the standard methods for hydrophobing silanol functional surfaces, including reaction with trimethylsilylating agents such as hexamethyldisiloxane or hexamethyldisilazane, If hydrophobing is conducted prior to reaction with the reagent comprising the catalytic group, the hydrophobing should not react all surface silanols, and should leave sufficient silanols unreacted as to allow reaction with the reagent comprising the catalytic group to an extent sufficient to provide high catalytic activity for the resulting catalyst. Prior to hydrophobing, the MCF is preferably dried, for example by heating in a vacuum (e.g. above about 150° C.) for a suitable time, or by drying in toluene using a Dean-Stark apparatus. The hydrophobing reaction may be conducted in a dry solvent, e.g. dry toluene. It may be conducted between about 10 and 100° C., or between about 10 and 50, 10 and 20, 20 and 100, 50 and 100, 50 and 70 or 20 and 40° C., for example at about 10, 15, 20, 25, 30, 35, 40, 45, 50, 55, 60, 65, 70, 75, 80, 85, 90, 95 or 100° C. Hydrophobing is preferably conducted using a hydrophobing reagent (e.g. trimethylsilylating agent) such as hexamethyldisilazane or chlorotrimethylsilane.

The process may also comprise reacting the support with a chiral modifying agent. The chiral modifying agent may comprise a chiral modifier, as described earlier, and may be capable of reacting with silanol groups on the MCF, for example through reactive groups such as dimethylchlorosilyl or dimethylallylsilyl as described earlier, or through trialkoxysilyl groups, such as trimethoxysilyl, triethoxyl etc. There may be a linker group between the chiral modifier and the reactive group, for example an alkylene (e.g. C3 to C10 straight chain, alicyclic or branched group or C1 or C2) or an arylene group or a functional group (e.g. a urea, an amide, an ester, an ether etc.) or a combination of these. The linker group may optionally be substituted. The reaction of the support with the chiral modifying agent may be conducted in solution, for example in dry solution, and may be conducted at a temperature between about 20 and about 110° C., and may be conducted at reflux in the solvent of the solution. A suitable solvent for the reaction is toluene. It may be conducted in the presence of an acid catalyst. The acid catalyst may be present at about 1 and about 10% w/w or w/v, or between about 1-5, 1-2, 5-10, 2-8, 2-5, 2-3, 3-5, 5-8, 4-8 or 3-7%, for example about 1, 2, 3, 4, 5, 6, 7, 8, 9 or 10% w/w or w/v. The acid catalyst may be soluble in the solvent. It may be for example p-toluenesulfonic acid, trifluoroacetic acid, trichloroacetic acid or some other acid. It may be an organic acid. The acid may be soluble in the solvent.

The reagent comprising the catalytic group may, as noted above, comprise an imidazolidin-4-one. Such compounds may be synthesised from amino acids, or derivatives thereof. The amino acids are 2-aminoalkanoic acids. The amino acids may be any of the naturally occurring amino acids, or may be synthetic amino acids. The amino acid may have a side chain capable of being converted into (or coupled with or elaborated to) a spacer group terminated by a reactive group, said reactive group being capable of reacting with silanol groups on MCF. Suitable amino acids include tyrosine and phenylalanine. The amino acid side chain may determine the substituent on the carbon adjacent the ring carbonyl of the imidazolidin-4-one, or may be converted into that substituent. The stereochemistry of the carbon atom adjacent the carbonyl of the amino acid may be the same as the stereochemistry of the carbon adjacent the ring carbonyl of the imidazolidin-4-one. Thus the amino acid may be converted into the corresponding methyl ester hydrochloride by known chemistry (or may be obtained in the form of the methyl ester hydrochloride). It will be understood that other esters may also be used. The other esters may include for example C1 to C6 straight chain, cyclic or branched chain esters such as ethyl, isopropyl, butyl, tertiary butyl, pentyl, neopentyl, hexyl or cyclohexyl. The ester may be converted into the corresponding N-substituted amide by reaction with a primary amine, where the substituent on the amine is retained in the amide, and ultimately is retained as the substituent on the amide nitrogen of the imidazolidin-4-one. The substituent may be for example an alkyl (e.g. C1 to C6 straight chain, branched chain or cyclic alkyl), aryl or arylalkyl group, or may be a group capable of coupling to the support, or a precursor to such a group. Conversion to the amide may be effected in solution, for example in alcohol solution. It may be conducted at room temperature, or at some other convenient temperature. It is preferably conducted at a temperature that is not sufficiently high that loss of the amine by evaporation does not interfere with the reaction. The temperature may be between about 10 and about 50° C., or between about 10 and 30, 20 and 50, 30 and 50 or 20 and 40° C., for example about 10, 20, 30, 40 or 50° C., but may be greater than 50 or less than 10° C. The reaction time may depend on the temperature of the reaction. It may depend on the nature of the amine (e.g. the steric hindrance of the amine). It may be between about 1 hour and 48 hours, or between about 12 hours and 48 hours, 24 and 48 hours, 12 hours and 24 hours, 6 and 24 hours, 18 and 30 hours or 6 and 18 hours, for example about 1, 2, 3, 4, 5, 6, 9, 12, 15, 18, 21, 24, 30, 36, 42 or 48 hours. It may be greater than 48 hours. Reaction of the resulting amino acid amide with a carbonyl compound generates the imidazolidin-4-one ring, wherein the substituents on the carbonyl carbon atom are the same as those on the carbon atom between the two nitrogen atoms of the resulting imidazolidin-4-one ring. The substituents may, independently, be for example hydrogen, an alkyl (e.g. C1 to C6 straight chain, branched chain or cyclic alkyl), aryl or arylalkyl group, and may be the same or different. The carbonyl compound may be an aldehyde or a ketone. Reaction with the carbonyl compound may be conducted in solution, for example in alcohol (e.g. methanol) solution. The reaction may be conducted at elevated temperature. It may be conducted at between 30 and about 100° C., or more than 100° C. The reaction temperature may depend on the boiling points of the carbonyl compound and of the solvent. The reaction may be conducted at between about 30 and 80, 30 and 60, 30 and 40, 50 and 100, 80 and 100, 40 and 80, 40 and 60 or 50 and 70° C., for example about 30, 40, 50, 60, 70, 80, 90 or 100° C. The reaction time may depend on the reaction temperature. It may be between about 1 hour and 48 hours, or between about 12 hours and 48 hours, 24 and 48 hours, 12 hours and 24 hours, 6 and 24 hours, 18 and 30 hours or 6 and 18 hours, for example about 1, 2, 3, 4, 5, 6, 9, 12, 15, 18, 21, 24, 30, 36, 42 or 48 hours. It may be greater than 48 hours.

Depending on the nature of the various substituents on the imidazolidin-4-one ring, elaboration of one or other of these substituents by known chemical reactions may provide a spacer group terminated by a reactive group, said reactive group being capable of reacting with silanol groups on MCF. A suitable reactive group may be a dimethylallylsilyl group.

If the C5 substituent of the ring is substituted with a phenolic group (e.g. 4-hydroxyphenylmethyl), a dimethylallylsilyl group may be attached to that substituent by reaction with a proton abstracting reagent (e.g. hydride) followed by an appropriate allylsilyl functional reagent, for example allyl bromobutyl dimethylsilane, in order to form an allylsilyl functional imidazolidin-4-one reagent. Reaction of an imidazolidin-4-one having a C5 phenolic substituent with a proton abstracting reagent may be conducted in a dipolar aprotic solvent such as DMF. The reaction is conveniently conducted with about a 10% molar excess of proton abstracting reagent (e.g. sodium hydride). The reaction temperature may be sub-ambient, and may be between about −10 and 10° C., or between about −10 and 0, 0 and 10, −5 and 5 or −2 and 2° C., for example between about −10, −8, −6, −4, −2, 0, 2, 4, 6, 8 or 10° C. The reaction time may depend on the reaction temperature, and may be between about 1 and 5 hours or more, and may be between about 1 and 3, 3 and 5, 2 and 4 or 2 and 5 hours, and may be about 1, 2, 3, 4 or 5 hours or more than 5 hours. The subsequent reaction with the allyllsilyl functional reagent may be conducted without separation of any intermediate products. Thus the reaction mixture from reaction of the imidazolidin-4-one with the proton abstracting reagent may be warmed to the desired reaction temperature. The reaction temperature may be room temperature or may be an elevated temperature. The reaction temperature may be between about 10 and about 50° C., or between about 10 and 30, 20 and 50, 30 and 50 or 20 and 40° C., for example about 10, 20, 30, 40 or 50° C., but may be greater than 50 or less than 10° C. The reaction time may depend on the temperature of the reaction. It may be between about 1 and 24 hours or more than 24 hours. It may be between about 1 and 12, 1 and 6, 1 and 3, 6 and 24, 12 and 24, 3 and 12, 2 and 9, 3 and 6 or 4 and 6 hours, and may be about 1, 2, 3, 4, 4.5, 5, 5.5, 6, 7, 8, 9, 10, 11, 12, 15, 18, 21 or 24 hours.

If the N3 substituent is hydroxyfunctional (for example hydroxyalkyl), a dimethylallylsilyl group may be attached to that substituent by reaction with a proton abstracting reagent (e.g. hydride) followed by an appropriate allylsilyl functional reagent, for example allyl bromobutyl dimethyl silane, in order to form an allylsilyl functional imidazolidin-4-one reagent. Reaction of an imidazolidin-4-one having N3 hydroxyfunctional substituent may be conducted in a similar manner to reaction of an imidazolidin-4-one having a C5 phenolic substituent, as described above.

Reaction of the allylsilyl functional imidazolidin-4-one reagent (which may have the allylsilyl group coupled to the imidazolidin-4-one ring through either C5 or N3) may be effected by reaction with MCF, optionally partially trimethylsilylated, using an acid catalyst. Thus the MCF is conveniently dried. This may be accomplished by heating in a vacuum overnight. The temperature may be between about 80 and 250° C., and should not be sufficiently high to affect the trimethylsilyl groups on the surface, if present. The temperature may be between about 80 and 200, 80 and 150, 80 and 120, 100 and 200, 150 and 250, 200 and 250, 150 and 200 or 170 and 200° C., for example about 80, 90, 100, 110, 120, 130, 140, 150, 160, 170, 180, 190, 200, 210, 220, 230, 240 or 250° C. The absolute pressure of the vacuum may be between about 0.01 and 100 mmHg, or between about 0.01, and 10, 0.01 and 1, 0.01 and 0.1, 0.1 and 100, 0.01 and 1, 1 and 10, 0.05 and 5, 0.1 and 1 or 0.5 and 5 mmHg, or example about 0.01, 0.05, 0.1, 0.5, 1, 2, 3, 4, 5, 6, 7, 8, 9, 10, 50 or 100 mmHg. The time for drying may be between about 6 and 24 hours, or between about 6 and 12, 12 and 24 or 12 and 18 hours, for example about 6, 9, 12, 15, 18, 21 or 24 hours or more than 24 hours.

Following drying of the MCF, reaction with the allylsilyl functional imidazolidin-4-one reagent may be conducted in a solvent, for example toluene or xylene. The solvent may conveniently be dried before use, by methods well known in the art. The MCF may be mixed with the solvent, the allylsilyl functional imidazolidin-4-one reagent, and an acid catalyst added, or some other convenient order of addition may be used. It is preferred that the MCF be combined with the solvent before addition of either the catalyst of the reagent. The reaction may be conducted at elevated temperature, for example between about 40 and 120° C., or between about 40 and 100, 4 and 80, 60 and 120, 80 and 120, 100 and 120, 90 and 110 or 95 and 105° C., for example 40, 50, 60, 70, 80, 90, 95, 100, 105, 110, 115 or 120° C. The reaction may be conducted for at least about 12 hours, or at least about 18 or 24 hours, or between about 12 and 48 hours, 12 and 36, 12 and 24, 24 and 48, 36 and 48, 12 and 36 or 18 and 30 hours, for example about 12, 15, 18, 19, 20, 21, 22, 23, 24, 25, 26, 27, 28, 29, 30, 36, 42 or 48 hours or more than 48 hours. Following that time, the catalyst may be filtered or otherwise removed from the reaction solution. It may be then washed with one or more solvents (e.g. methanol, ethanol, dichloromethane, acetone etc.), either together or sequentially, and dried. Drying is conveniently conducted under vacuum. The absolute pressure of the vacuum may be between about 0.01 and 100 mmHg, or between about 0.01, and 10, 0.01 and 1, 0.01 and 0.1, 0.1 and 100, 0.01 and 1, 1 and 10, 0.05 and 5, 0.1 and 1 or 0.5 and 5 mmHg, or example about 0.01, 0.05, 0.1, 0.5, 1, 2, 3, 4, 5, 6, 7, 8, 9, 10, 50 or 100 mmHg. The time for drying may be between about 6 and 24 hours, or between about 6 and 12, 12 and 24 or 12 and 18 hours, for example about 6, 9, 12, 15, 18, 21 or 24 hours or more than 24 hours. Drying may be conducted at room temperature or at some elevated temperature.

The heterogeneous catalyst of the present invention may be used to catalyse a reaction of at least one starting material to produce a product by either a Friedel-Craft or a Diels-Alder reaction. It will be understood that, depending on the nature of the catalytic group of the catalyst, the catalyst may be capable of catalysing one or other of the above reactions, or may be capable of catalysing both of the reactions. Each reaction may be an intramolecular reaction, in which case the reaction may be conducted with a single starting material, or it may be an intermolecular reaction, in which case the reaction may be conducted with two starting materials. In the case of an intramolecular reaction, the stoichiometry of the two reacting portions is generally 1:1 on a molar basis although exceptions to this may occur. In the case of a two starting materials, the stoichiometry may be varied from 1:1 in order for example to improve conversion of the more expensive of the two starting materials. The stoichiometry may also vary from 1:1 if for example double addition is required (e.g. if one starting material comprises two isolated dienophiles and the other comprises a single diene, the optimum stoichiometry may be about 1:2 dienophile to diene).

The Friedel-Craft reaction may be a Friedel-Craft alkylation. It may be conducted in the presence of an acid, and the acid may be soluble in the reaction medium. The reaction medium may comprise a polar (e.g. water miscible) solvent, for example THF, acetonitrile, methanol, DMSO, acetone, DMF etc. and may comprise water. It may be conducted in some other solvent for example dichloromethane. The nature of the solvent and the concentration of the water may depend on the solvency required. There may be for example between about 0 and about 10% water (v/v) or between about 0 and 5, 0 and 2, 2 and 10, 5 and 10 or 2 and 7% water, e.g. about 0, 1, 2, 3, 4, 5 ,6 ,7 ,8, 9 or 10% water. An acid, which may be soluble in the mixture of solvent and water, may be added to the reaction medium. It may be a strong acid. It may be an organic or an inorganic acid. It may be for example trifluoroacetic acid. The concentration of the acid may be between about 1 and about 50 mM, or between about 1 and 20, 1 and 10, 1 and 5, 5 and 50, 10 and 50, 20 and 50, 5 and 20, 5 and 10 or 7 and 9 mM, and may be about 1, 2, 3, 4, 5, 6, 7, 8, 9, 10, 15, 20, 25, 30, 35, 40, 45 or 50 mM. In one method for conducting the reaction, the catalyst is combined with the reaction medium and the acid. The ratio of catalyst to reaction medium may be between about 1:10 and about 1:50 w/v, or some other suitable ratio. The ratio may be between about 1:10 and 1:40, 1:10 and 1:30, 1:10 and 1:20, 1:20 and 1:40, 1:15 and 1:30 or 1:15 and 1:20, and may be about 1:10, 1:15, 1:16, 1:17, 1:18, 1:19, 1:20, 1:25, 1:30, 1:35, 1:40, 1:45 or 1:50. A first starting material, an aromatic substrate, is then added. The ratio of the first starting material to the catalytic groups of the catalyst may be between about 200:1 and about 10:1, or between about 200:1 and 50:1, 200:1 and 100:1, 100:1 and 10:1, 50:1 and 10:1, 80:1 and 30:1, 70:1 and 40:1 or 60:1 and 50:1, and may be about 10:1, 20:1, 30:1, 40:1, 45:1, 50:1, 55:1, 60:1, 70-:1, 80:1, 90:1, 100:1, 120:1, 140:1, 160:1, 180:1 or 200:1. The reaction medium together with the heterogeneous catalyst and the acid co-catalyst maybe stirred during the addition. The second starting material, a reagent, may then be added. It may be added in a ratio to the first reagent of between about 1:1 and about 3:1, or between about 1:1 and 2:1, 2:1 and 3:1 or 1.5:1 and 2.5:1, for example about 1:1, 1.1:1, 1.2:1, 1.3:1, 1.4:1, 1.5:1, 2:1, 2.5:1 or 3:1. The reaction may be maintained at room temperature, or at some other convenient temperature (e.g. between about 0 and 50° C., for example about 10, 20, 30, 40 or 50° C. or some other temperature). In some reactions, the temperature may be as low as about −50° C., or −40, −30, −20, −10 or 0° C. The reaction may be conducted under air, or in the absence of oxygen, for example under nitrogen, argon, helium or carbon dioxide. The reaction may be monitored, e.g. by tlc, hplc, gc, uv spectroscopy, ir spectroscopy, nmr spectroscopy or some other suitable method. Once the desired level of conversion is achieved (e.g. 80, 85, 90, 95, 96, 97, 98, 99 or 100%), the catalyst may be separated from the reaction medium by filtration, centrifugation or some other suitable method. The product may be isolated from the liquid phase and purified using methods well known in the field of organic chemistry.

The Diels-Alder reaction may be conducted in the presence of an acid, and the acid may be soluble in the reaction medium. The reaction medium may comprise a polar (e.g. water miscible) solvent, for example THF, acetonitrile, methanol, DMSO, acetone, DMF etc. and may comprise water. It may be conducted in some other solvent for example dichloromethane. The nature of the solvent and the concentration of the water may depend on the solvency required. There may be for example between about 0 and about 10% water (v/v) or between about 0 and 5, 0 and 2, 2 and 10, 5 and 10, 2 and 4 or 2 and 7% water, e.g. about 0, 1, 2, 3, 4, 5, 6, 7, 8, 9 or 10% water. An acid, which may be soluble in the mixture of solvent and water, may be added to the reaction medium. It may be a strong acid. It may be an organic or an inorganic acid. It may be for example trifluoroacetic acid. The concentration of the acid may be between about 1 and about 50 mM, or between about 1 and 20, 1 and 10, 1 and 5, 5 and 50, 10 and 50, 20 and 50, 5 and 20, 5 and 10 or 4 and 6 mM, and may be about 1, 2, 3, 3.5, 4, 4.5, 5, 5.5, 6, 6.5, 7, 8, 9, 10, 15, 20, 25, 30, 35, 40, 45 or 50 mM. In one method for conducting the reaction, the catalyst is combined with the reaction medium and the acid. The ratio of catalyst to reaction medium may be between about 1:10 and about 1:50 w/v, or some other suitable ratio. The ratio may be between about 1:10 and 1:40, 1:10 and 1:30, 1:10 and 1:20, 1:20 and 1:40, 1:25 and 1:35, 1:15 and 1:30 or 1:15 and 1:20, and may be about 1:10, 1:15, 1:16, 1:17, 1:18, 1:19, 1:20, 1:25, 1:30, 1:35, 1:40, 1:45 or 1:50. A first starting material, a dienophile, is then added. The ratio of the first starting material to the catalytic groups of the catalyst may be between about 200:1 and about 5:1, or between about 200:1 and 10:1, 200:1 and 50:1, 200:1 and 100:1, 100:1 and 10:1, 50:1 and 10:1, 40:1 and 10:1, 30:1and 10:1 or 25:1 and 15:1, and may be about 10:1, 15:1, 16:1, 17:1, 18:1, 19:1, 20:1, 21:1, 22:1, 23:1, 24:1, 25:1 30:1, 40:1, 50:1, 60:1, 70:1, 80:1, 90:1, 100:1, 120:1, 140:1, 160:1, 180:1 or 200:1. The reaction medium together with the heterogeneous catalyst and the acid co-catalyst maybe stirred during the addition. The second starting material, a diene, may then be added. It may be added in a ratio to the first reagent of between about 1:1 and about 3:1, or between about 1:1 and 1.5:1, 1:1 and 2:1, 2:1 and 3:1 or 1.5:1 and 2.5:1, for example about 1:1, 1.1:1, 1.2:1, 1.3:1, 1.4:1, 1.5:1, 2:1, 2.5:1 or 3:1. The reaction may be maintained at room temperature, or at some other convenient temperature (e.g. between about 0 and 50° C., for example about 10, 20, 30, 40 or 50° C. or some other temperature). In some reactions. the temperature may be as low as about −50° C., or −40, −30, −20, −10 or 0° C. The reaction may be conducted under air, or in the absence of oxygen, for example under nitrogen, argon, helium or carbon dioxide. The reaction may be monitored, e.g. by tlc, hplc, gc, uv spectroscopy, ir spectroscopy, nmr spectroscopy or some other suitable method. Once the desired level of conversion is achieved (e.g. 80, 85, 90, 95, 96, 97, 98, 99 or 100%), the catalyst may be separated from the reaction medium by filtration, centrifugation or some other suitable method. The product may be isolated from the liquid phase and purified using methods well known in the field of organic chemistry.

EXAMPLES

Figure 1:
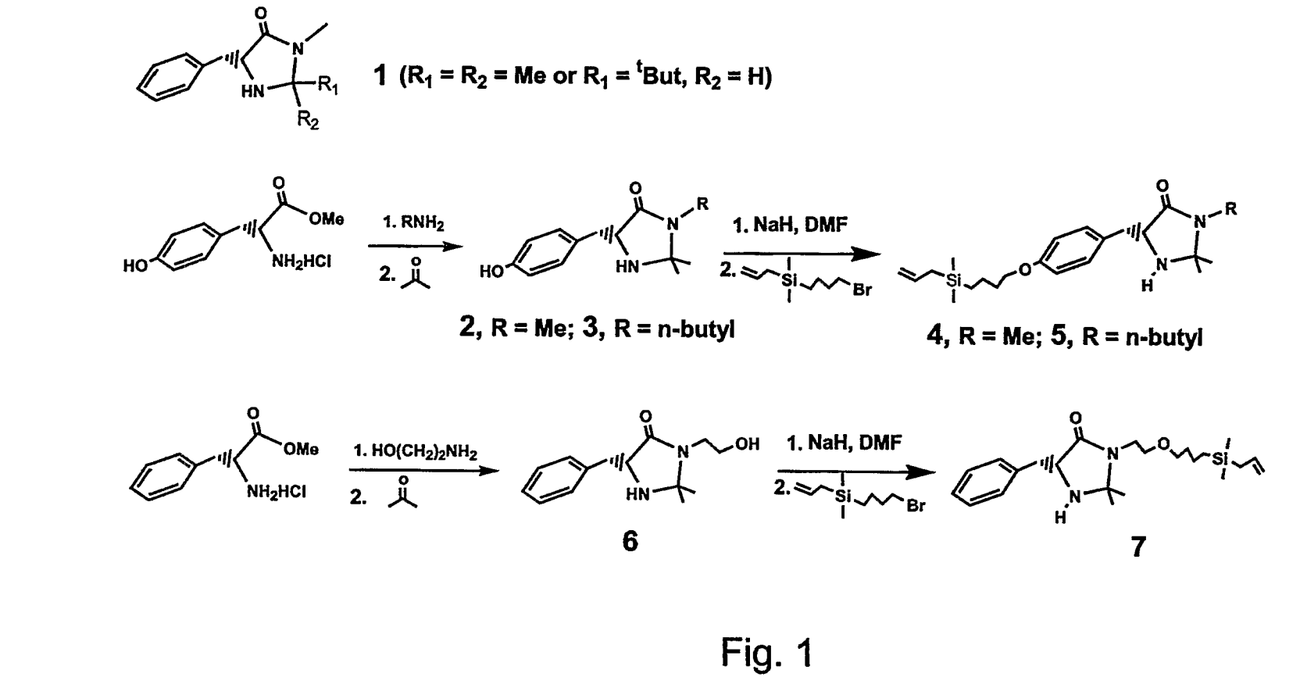
FIG. 1 shows the structure of a chiral imidazolidin-4-one catalyst, and shows a scheme for synthesising a reagent comprising a catalytic group, for use in making a heterogeneous catalyst according to the present invention.
Figure 2:
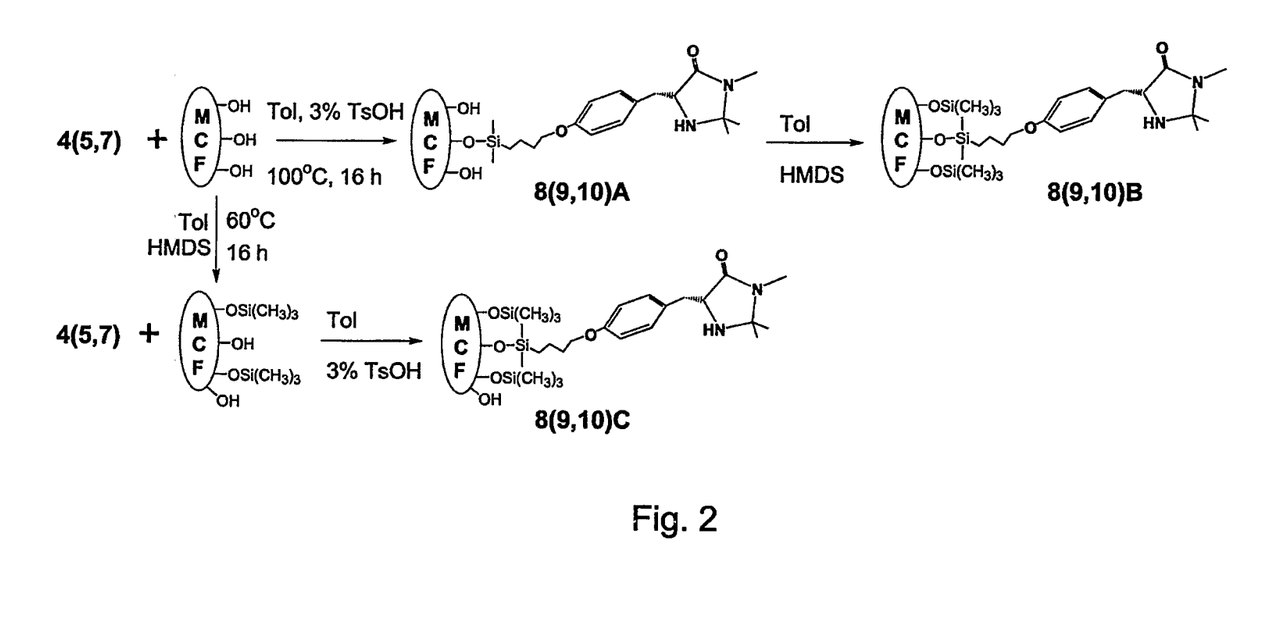
FIG. 2 shows a scheme which illustrates two different routes to heterogeneous catalysts according to the present invention.

To immobilize the organocatalyst onto MCF, the aryl residue and the amide nitrogen atom of 1 were modified for building different linkages (FIG. 1). The characteristics of the linkages, such as flexibility and length, could be critical to the reactivity of the heterogenized catalysts. Starting from (S)-tyrosine methyl ester hydrochloride, the imidazolidinone 2 and 3 were easily obtained in 80-82% yield. On the other hand, (S)-phenylalanine reacted with ethanolamine and then acetone to generate imidazolidinone 6, with the ethylene hydroxyl group anchored on the amide nitrogen. The phenolic group in 2 and 3, and the hydroxy group in 6 were functionalized by allylsilane through an O-alkylation process to give 4, 5 and 7, respectively, in good yields. Finally, 4, 5, 7 were anchored onto MCF surface to generate the supported catalysts 8, 9 and 10 respectively (see FIG. 2). The inventors have, surprisingly, found that using 3-5% p-toluenesulfonic acid (p-TsOH) as catalyst, the allylsilane immobilization method could be extended to various types of silica supports. Generally, deallylation reaction between allylsilane and alcohol or silanol needs to be catalyzed by acid:

Without an acid catalyst, significant reaction can be achieved only with silica samples with acidic surface, such as FSM-16. By adding 2-5% acid catalyst, high silane loading could be achieved with various types of silica, even when the reaction was run at room temperature.

It is known that the silanol groups on the silica surface affects the activity of the immobilized catalyst. The silanols are capable of interacting with active sites of the catalyst, such as through hydrogen bonding or proton migration in the case of organocatalysts. They may also catalyze certain side-reactions. In an effort to examine the relationship between the catalyst performance and the MCF surface environment, heterogenized catalysts A, B and C were developed with the use of different MCF surface modification schemes (see FIG. 2). In all cases, spherical MCF microparticles of 2-10 μm were used as the support. These microparticles have a BET surface area of 504 m²/g, a cell-like pore size of 22 nm, and a window size of 13 nm. A was obtained from one-step immobilization onto the MCF support with uncapped silanols. B was derived by post-capping of MCF silanols with hexamethyldisilazane (HMDS) after the catalyst immobilization. C was obtained by immobilizing the catalyst onto a MCF support whose silanols had been partially pre-capped with trimethylsilyl (TMS) groups (0.6-0.8 mmol/g) using a controlled amount of HMDS.

Figure 3:
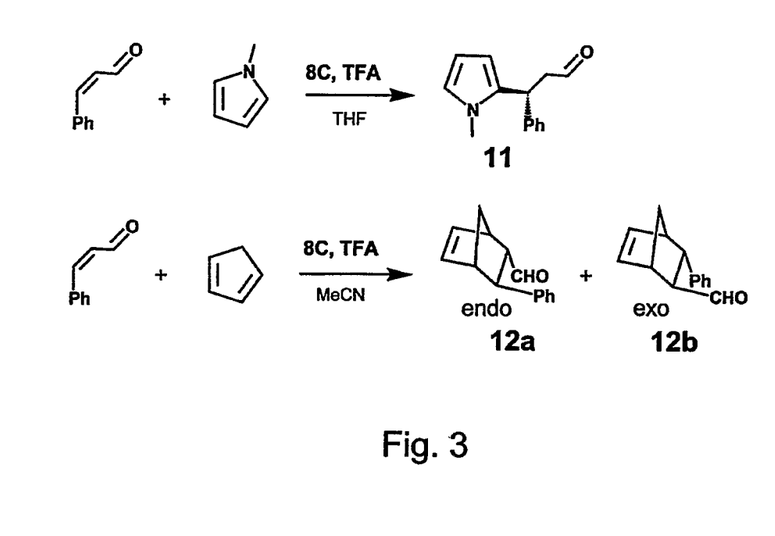
FIG. 3 shows reaction schemes for Friedel-Craft and Diels-Alder reactions catalysed by a heterogeneous catalyst of the present invention.

The MCF-supported chiral amine catalysts A-C were first studied for the asymmetric Friedel-Crafts alkylation, one of the most important C-C bond forming reaction (see FIG. 3). Prior to this study, there were reports of polymer- and silica-supported imidazolidinone-based catalysts, but they were not used for Friedel-Crafts alkylation. There has been very limited literature on heterogeneous asymmetric Friedel-Crafts alkylation in general. Table 1 shows that the MCF-supported catalysts were similar in reactivity to unsupported imidazolidinone. However, their enantioselectivity and recyclability strongly depended on the MCF surface modification. Catalyst 8A gave a good yield, but a lower enantiomeric excess (ee) (67%) compared with the unsupported catalyst (82%). It was found that the catalyst loadings on MCF (0.1-0.4 mmol/g) did not significantly affect the properties of the supported catalysts. The enantioselectivity of 8A was reduced considerably upon reuse. To retain the activity of the supported catalyst, about 20% additional trifluoroacetic acid (TFA) should be introduced, possibly to counter the effect of TFA leaching during catalyst washes.

Catalyst 8B was post-capped with TMS groups after the immobilization of 4. Relative to the uncapped catalyst 8A, catalyst 8B showed slightly better enantioselectivity and recyclability. Catalyst 8C, which was partially pre-capped with TMS prior to the immobilization of 4, demonstrated superior enantioselectivity and reusability compared to catalysts 8A and 8D (see Table 1, Entry 10-13). This may have been due to the fact that organocatalysts derived from 4 were more well-dispersed throughout the porous support and better separated from each other when they were loaded onto partially pre-capped MCF support. An ee value as high as 92% was achieved with catalyst 8C when the reaction was run at −30° C. (Table 1; Entry 14). However, a low yield (21%) was noted possibly due to the high viscosity of the THF-H₂O solvent mixture at the low temperature.

Besides manipulating the surface chemistry of the MCF support, the inventors also attempted to modify the linkage chemistry of the organocatalyst (the catalytic group). For example, the linker group was attached to the amide group (instead of the phenyl group) of 1 in the case of 7 (in contrast to 4 and 5). Catalyst 7 was found to exhibit a higher enantioselectivity (90%) (Table 2, Entry 4) in homogeneous Friedel-Crafts reaction than the original MacMillan's catalyst (catalyst 2) (81%) (Table 1, Entry 1). However, its heterogenized counterpart, catalyst 10C showed lower activity and significantly reduced enantioselectivity. This indicates that the alkyl spacer group attached to the amide nitrogen did not impact the catalytic properties significantly in the homogeneous reaction, but the linker had adverse effect on the organocatalyst's enantioselectivity when it was involved in the catalyst immobilization onto the MCF support. In contrast, although lower in enantioselectivity than their original homogeneous catalysts (2 and 3, respectively), the heterogenized catalysts 8C and 9C still demonstrated good enantioselectivities. This suggested that attaching the homogeneous catalysts through a linker group at the phenyl group of 1 would minimize any adverse impact in heterogenizing the organocatalysts for the Friedel-Crafts alkylation reaction.

The Diels-Alder cycloaddition reaction (FIG. 3) was also studied to compare the MCF-supported catalysts to the other heterogenized catalysts. Table 3 shows that the MCF-supported catalysts 8C and 10C (Entries 4, 5, 7 and 8) provided almost as high enantioselectivities and similar regioselectivities as the polymer- and silica gel-supported catalysts (Entries 11-13), but much higher chemical activities. These heterogenized catalysts (8C and 10C) gave rise to the high yields achieved by the homogeneous catalysts (2 and 7) with slightly longer reaction times. Whereas the polymer- and silica gel-supported catalysts only produced moderate or poor yields even with higher catalyst loading or much longer reaction time. These findings illustrated the benefits of the three-dimensional interconnected pore structure, ultralarge pore size, and high surface area of siliceous MCF. Organocatalysts were also known in many cases to be robust to air and moisture, but sensitive to the matrix of the reaction system, such as acids or bases. Thus, providing a clean and well-controlled catalyst environment via a direct one-step catalyst immobilization scheme and an effective support surface modification is crucial in the successful development of heterogenized organocatalysts.

Figure 4:
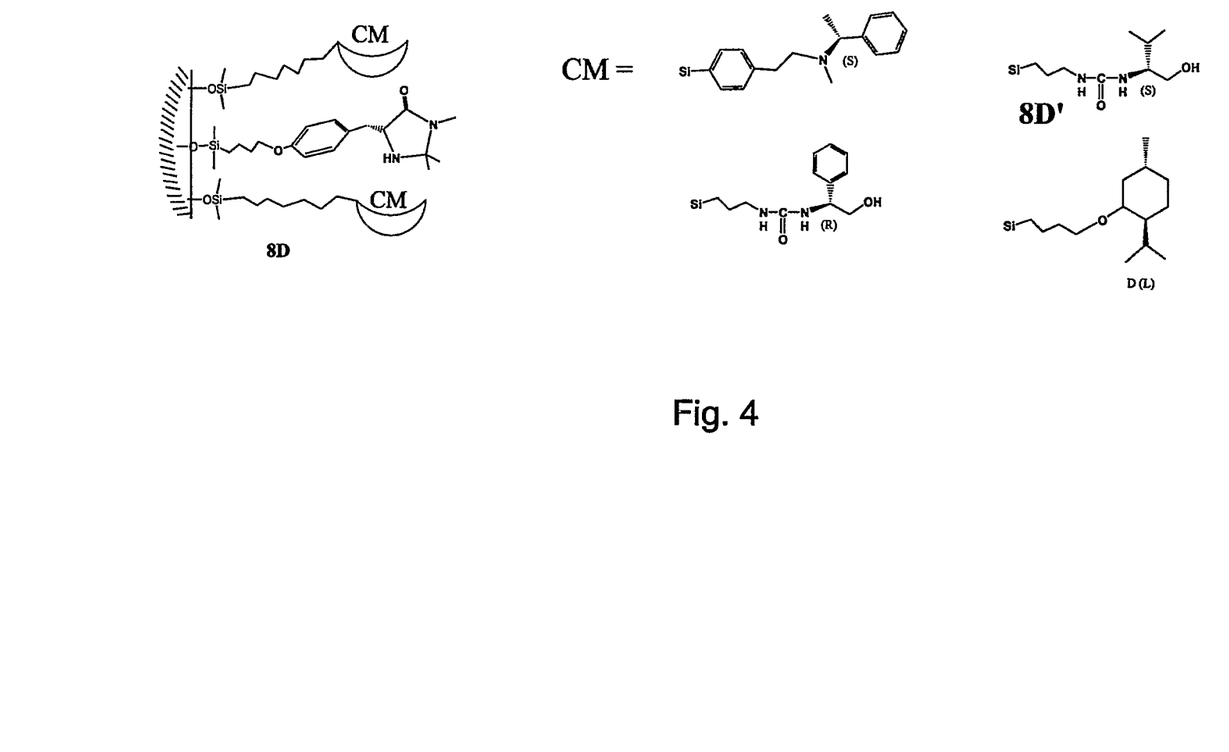
FIG. 4 shows the structure of a heterogeneous catalyst according to the present invention, wherein the catalyst has chiral modifiers coupled thereto.

Additionally, the inventors have attempted to introduce chiral microenvironment in the heterogenized organocatalysts by modifying the MCF support surface with chiral auxiliaries. Amplification and/or transfer of chirality from chiral environment to reaction systems are of great interest and challenge. In the present study, various chiral molecules (CM) with different linkages were introduced onto the MCF surface prior to the immobilization of 4 (see FIG. 4). The combined loading for catalyst 4 (0.2 mmol/g) and chiral modifier 8D' (0.8 mmol/g) was 1.0 mmol/g. Thus, the average center-to-center distance between the loaded molecules was 0.9 nm. Given their high loadings and close proximity, interactions may be expected between the CM and organocatalysts. Table 3 shows that catalyst 8D (which was not TMS-capped, but pre-loaded with 8D') (Entries 9 and 10) gave similar enantioselectivity and regioselectivity as catalyst 8C (which was partially pre-capped with TMS) (Entries 4 and 5), but better selectivities than 8A (which was not TMS-capped) (Entries 2 and 3). The findings suggested that the CM modification of the support surface may have a similar effect to TMS capping of the silanol groups.

Experimental Section

Synthesis of catalyst 8C. MCF was dried under vacuum at 180° C. for 16 h. Dry toluene (30 mL) and HMDS (293 mg, 1.8 mmol) were added to the dried MCF (5 g), and the resulting suspension was stirred at 60° C. for 16 h. The mixture was filtered, and the solid was washed successively with methanol, acetone and dichloromethane. After drying in vacuum overnight, the partially TMS-capped MCF (5.26 g) was collected and characterized by IR and elemental analysis (C, H, N). The loading of TMS groups was 0.67 mmol/g based on elemental analysis and weight gain analysis. The modified MCF (5.26 g) was dried under vacuum at 85° C. overnight. Toluene (30 mL), catalyst precursor 4 (972 mg, 2.5 mmol) and p-TsOH (8.5 mg, 0.05 mmol) were then added to the modified MCF sequentially. The suspension was stirred at 100° C. for 24 h. The mixture was then filtered, and the solid was washed thoroughly with methanol, acetone and dichloromethane. After drying in vacuum, catalyst 8C (5.50 g) was collected and characterized by IR and elemental analysis. The loading of 4 was 0.14 mmol/g based on elemental analysis and weight gain.

Friedel-Crafts alkylation (Table 1, Entry 10). MCF-supported catalyst 8C (0.5 g, 0.07 mmol) was treated with THF (8 ml), $H_2O$ (0.5 mL) and aqueous TFA solution (0.5 M, 140 μL, 0.07 mmol). The mixture was stirred for 10 min, and then N-methylpyrrole (310 μL, 3.5 mmol) was added. Next, trans-cinnamaldehyde (88 μL, 0.7 mmol) was dripped into the reaction vial. The suspension was stirred at room temperature, and the reaction was monitored by thin layer chromatography (TLC). The suspension was centrifuged, and the solution was decanted. This procedure was repeated at least three times using THF as the washing solvent. The solid catalyst was used directly for the next run. The combined solution was prepared following literature procedure to give a pure alcoholic product in 72% yield (108 mg, 0.5 mmol). The $^1H$ NMR data were in agreement with those reported previously. Enantioselectivity was determined by gas liquid chromatography (GLC) analysis of the corresponding aldehyde (Chiraldex Γ-TA column, 0.25 mm×30 m, 5° C./min ramp from 70° C. to 170° C., 23 psi); R isomer: $t_r$=26.6 min, and S isomer: $t_r$=27.4 min.

TABLE 1

Comparison of catalysts derived from 2 in the synthesis of 11.

| Entry | Catalyst | Run # | Loading (mol %) | TFA | Time (h) | Yield[a] (%) | ee[b] (%) |
|---|---|---|---|---|---|---|---|
| 1 | 2 | 1 | 20 | 1 | 3 | 78 | 81 |
| 2 | 2 | 1 | 10 | 1 | 8 | 76 | 82 |
| 3 | 8A[c] | 1 | 10 | 1 | 6 | 71 | 65 |
| 4 | 8A[d] | 1 | 10 | 1 | 6 | 72 | 67 |
| 5 |  | 2 | 10 | 1 | 5 | 70 | 52 |
| 6 |  | 2[e] | 10 | 0 | 16 | 68 | 60 |
| 7 |  | 2[e] | 10 | 0.2 | 8 | 69 | 59 |
| 8 | 8B | 1 | 10 | 1 | 6 | 71 | 68 |
| 9 |  | 2 | 10 | 0.2 | 8 | 70 | 64 |
| 10 | 8C | 1 | 10 | 1 | 6 | 72 | 74 |
| 11 |  | 2 | 10 | 0.2 | 8 | 70 | 70 |
| 12 |  | 3 | 10 | 0.2 | 8 | 69 | 69 |
| 13 |  | 4 | 10 | 0.2 | 8 | 69 | 68 |
| 14 | 8C[f] | 1 | 10 | 1 | 72 | 21 | 92 |

[a]Yields based upon isolation of the corresponding alcohol after $NaBH_4$ reduction.
[b]Product ratios determined by chiral gas chromatography (GC) (chiraldex Γ-TA).
[c]The catalyst loading was 0.20 mmol/g of MCF.
[d]The catalyst loading was 0.37 mmol/g of MCF.
[e]Second run of a different batch.
[f]Reaction was run at −30° C.

TABLE 2

Comparison of catalysts derived from 3 and 7 in the synthesis of 11.

| Entry | Catalyst | Run # | Loading (mol %) | TFA | Time (h) | Yield[a] (%) | ee[b] (%) |
|---|---|---|---|---|---|---|---|
| 1 | 3 | 1 | 20 | 1 | 3 | 77 | 80 |
| 2 | 9C | 1 | 10 | 1 | 6 | 72 | 71 |
| 3 |   | 2 | 10 | 1 | 8 | 69 | 65 |
| 4 | 7 | 1 | 20 | 1 | 4 | 78 | 90 |
| 5 | 10C | 1 | 10 | 1 | 8 | 60 | 40 |

[a]Yields based upon isolation of the corresponding alcohol after NaBH$_4$ reduction.
[b]Determined by chiral GC (chiraldex Γ-TA).

TABLE 3

Comparison of catalysts derived from 2 and 7, and polymer-supported and silica gel-supported catalysts in the syntheses of 12a and 12b.

| Entry | Catalyst | Run # | Loading (mol %) | TFA | Time (h) | Yield[a] (%) | Exo:Endo Ratio[b] | ee[c] (%) |
|---|---|---|---|---|---|---|---|---|
| 1 | 2 | 1 | 5 | 1 | 24 | 99 | 1.3:1 | 93/93[c] |
| 2 | 8A | 1 | 5 | 1 | 30 | 93 | 1.3:1 | 73/74 |
| 3 |   | 2 | 5 | 1 | 44 | 96 | 1.3:1 | 63/67 |
| 4 | 8C | 1 | 5 | 1 | 30 | 93 | 1.3:1 | 83/87 |
| 5 |   | 2 | 5 | 1 | 44 | 96 | 1.3:1 | 76/84 |
| 6 | 7 | 1 | 5 | 1 | 24 | 99 | 1.3:1 | 91/90 |
| 7 | 10C | 1 | 5 | 1 | 30 | 95 | 1.3:1 | 83/85 |
| 8 |   | 2 | 5 | 1 | 44 | 96 | 1.3:1 | 74/80 |
| 9 | 8D | 1 | 5 | 1 | 44 | 96 | 1.3:1 | 83/84 |
| 10 |   | 2 | 5 | 1 | 44 | 95 | 1.3:1 | 82/83 |
| 11 | PEG[d] | 1 | 10 | HBF$_4$ | — | 68 | 1.3:1 | 88/— |
| 12 | JandaJel[e] | 1 | 20 | HCl | 24 | 70 | 1.2:1 | 99/99 |
| 13 | Silica Gel[e] | 1 | 3.3 | HCl | 64 | 33 | 1:1.1 | 90/90 |

[a]Yields based upon isolated product or GC.
[b]Determined by $^1$H NMR.
[c]Determined by chiral GC (chiraldex β-PH).
[d]M. Benaglia, G. Celentano, M. Cinquini, A. Puglisi, F. Cozzi, *Adv. Synth. Catal.* 2002, 344, 149; A. Puglisi, M. Benaglia, M. Cinquini, F. Cozzi, G. Celentano, *Eur. J. Org. Chem.* 2004, 2004(3), 567.
[e]S. A. Selkala, J. Tois, P. M. Pihko, A. M. P. Koskinen, *Adv. Synth. Catal.* 2002, 344, 941.

Further Experimentation

General Information. All solvents were used as obtained from commercial suppliers, unless otherwise noted. Centrifugation was performed on Eppendorf Centrifuge 5810R (4000 rpm, 10 min). $^1$H NMR spectra were recorded on Brucker AV-400 (400 MHz) instrument. Data for $^1$H NMR were reported as chemical shift (δ ppm), multiplicity (s=singlet, d=doublet, t=triplet, q=quartet, m=multiplet). IR spectra were obtained with a Digilab FTS 7000 Series using a photoacoustic cell (MTEC Model 300). GC-MS was performed on Shimadzu GCMS QP2010. GLC was performed on Agilent 6890N Series gas chromatograph equipped with a split-mode capillary injection system and flame ionization detector, using Bodman Chiraldex Γ-TA column (0.25 mm×30 m) or Bodman Chiraldex β-PH column (0.25 mm×30 m). C, H, N analyses were obtained with EAI CE440 Elemental Analyzer.

Progress of the Friedel-Crafts and Diels-Alder reactions were typically monitored by TLC analysis, or where necessary, by GC or GC-MS analysis.

Cyclopentadiene was cracked from the dimer before use. Other chemicals were is used as-received from the commercial suppliers. Synthesis of spherical MCF microparticles was described in S. S. Lee, Y. Han, J. Y. Ying (submitted to *Adv. Mater.*) TEM confirmed that the particle size and morphology of spherical MCF microparticles were not changed after the catalytic reactions.

Absolute configurations of 11 and 12 were assigned based on the literature (N. A. Paras, D. W. C. MaxMillan, *J. Am. Chem. Soc.* 2001, 123, 4370; K. A. Ahrendt, C. J. Borths, D. W. C. MaxMillan, *J. Am. Chem. Soc.* 2000, 122, 4243).

Synthesis of (5S)-5-(4-hydroxyl-benzyl)-2,2,3-trimethylimidazolidin-4-one (2). (S)-tyrosine methyl ester hydrochloride (23 g, 100 mmol) was added to an ethanolic solution of MeNH$_2$ (60 mL, 8 M), and the resulting mixture was stirred at room temperature for 24 h. The excess MeNH$_2$ was removed by distillation or by washing with THF several times until the N-methyl amide product was obtained as a white solid. Dry MeOH (200 mL) and dry acetone (40 mL) were added to this residue. The resulting solution was stirred at 60° C. for 24 h, cooled to room temperature, and then concentrated in vacuo. Compound 2 was obtained as a white solid in 82% overall yield (19.2 g, 82 mmol) after silica gel chromatography (1:1 of EtOAc:Hex). $^1$H NMR (CDCl$_3$): δ 7.09 (d, 2H), 6.74 (d, 2H), 3.82 (t, 1H), 3.06 (m, 2H), 2.78 (s, 3H), 1.32 (s, 3H), 1.22 (s, 3H). Elemental analysis for C$_{13}$H$_{18}$N$_2$O$_2$ (2)—calculated: C 66.64, H 7.74, N 11.96%; observed: C 66.24, H 7.70, N 12.10%.

Synthesis of (5S)-S-(4-hydroxyl-benzyl)-2,2-dimethyl-3-butylimidazolidin-4-one (3). (S)-tyrosine methyl ester hydrochloride (23 g, 100 mmol) was added to n-butylamine (79 mL, 800 mmol), and the resulting mixture was stirred at room temperature for 24 h. The excess butylamine was removed by distillation or by washing with THF several times until the N-butyl amide product was obtained as a white solid. Dry MeOH (200 mL) and dry acetone (40 mL) were added to this residue. The resulting solution was stirred at 60° C. for 24 h, cooled to room temperature, and then concentrated in vacuo. Compound 3 was obtained as a white solid in 80% overall yield (22.1 g, 80 mmol) after silica gel chromatography (1:1 of EtOAc:Hex). $^1$H NMR (CDCl$_3$): δ 7.08 (d, 2H), 6.76 (d, 2H), 3.78 (t, 1H), 3.32 (m, 1H), 3.08 (m, 2H), 2.94 (m, 1H), 1.51 (m, 2H), 1.33 (m, 2H), 1.31 (s, 3H), 1.20 (s, 3H), 0.95 (t, 3H). Elemental analysis for C$_{16}$H$_{24}$N$_2$O$_2$ (3)—calculated: C 69.53, H 8.75, N 10.14%; observed: C 69.01, H 8.66, N 10.76%.

Synthesis of (5S)-5-(4-allyldimethylsilylbutoxyl-benzyl)-2,2,3-trimethylimidazolidin-4-one (4). NaH (60% in oil, 480 mg, 12 mmol) was added to a DMF solution of 2 (2.34 g, 10 mmol) at 0° C. The resulting mixture was stirred for 3 h, and the ice bath was gradually warmed to room temperature.

Allylbromobutyldimethylsilane (11 mmol) was then added, and stirred for another 5 h. The solution was concentrated in vacuo at 65° C. to remove DMF. The residue was extracted with diethyl ether to remove the salts. Compound 4 was obtained as a colorless oil in 90% yield (3.50 g, 9 mmol) after silica gel chromatography (1:1 of EtOAc:Hex). $^1$H NMR (CDCl$_3$): δ 7.15 (d, 2H), 6.85 (d, 2H), 5.78 (m, 1H), 4.85 (m, 2H), 3.95 (t, 2H), 3.78 (t, 1H), 3.06 (t, 2H), 2.76 (s, 3H), 1.80 (m, 2H), 1.55 (d, 2H), 1.48 (m, 2H), 1.30 (s, 3H), 1.19 (s, 3H), 0.59 (m, 2H), 0.01 (s, 6H). Elemental analysis for C$_{22}$H$_{36}$N$_2$O$_2$Si (4)—calculated: C 67.99, H 9.34, N 7.21%; observed: C 68.50, H 9.45, N 7.20%.

Synthesis of (5S)-5-(4-allyldimethylsilylbutoxyl-benzyl)-2,2-dimethyl-3-butylimidazolidin-4-one (5). NaH (60% in oil, 480 mg, 12 mmol) was added to a DMF solution of 3 (2.76 g, 10 mmol) at 0° C. The resulting mixture was stirred for 3 h, and the ice bath was gradually warmed to room temperature. Allylbromobutyldimethylsilane (11 mmol) was then added and stirred for another 5 h. The solution was concentrated in vacuo at 65° C. to remove DMF. The residue was extracted with diethyl ether to remove the salts. Compound 5 was obtained as a colorless oil in 85% yield (3.66 g, 8.5 mmol) after silica gel chromatography (1:1 of EtOAc:Hex). $^1$H NMR (CDCl$_3$): δ 7.20 (d, 2H), 7.12 (d, 2H), 5.80 (m, 1H), 4.85 (m, 2H), 3.94 (t, 2H), 3.74 (m, 1H), 3.31 (m, 1H), 2.90-3.15 (m, 3H), 1.81 (m, 2H), 1.50-1.60 (m, 6H), 1.31 (m, 2H), 1.29 (s, 3H), 1.20 (s, 3H), 0.93 (t, 3H), 0.59 (m, 2H), 0.01 (s, 6H). Elemental analysis for C$_{25}$H$_{42}$N$_2$O$_2$Si (5)—calculated: C 69.72, H 9.83, N 6.50%; observed: C 69.43, H 9.66, N 6.87%.

Synthesis of (5S)-5-benzyl-2,2-dimethyl-3-(2-hydroxyl-ethyl)-imidazolidin-4-one (6). (S)-phenylalanine methyl ester hydrochloride (21.5 g, 100 mmol) was added to ethanolamine (48 mL, 800 mmol), and the resulting mixture was stirred at room temperature for 24 h. The excess ethanolamine was removed by distillation until the N-(2-hydroxylethyl) amide product was obtained as a white solid. Dry MeOH (200 mL) and dry acetone (40 mL) were added to this residue. The resulting solution was stirred at 60° C. for 24 h, cooled to room temperature, and then concentrated in vacuo. Compound 6 was obtained as a white solid in 55% overall yield (13.6 g, 55 mmol) after silica gel chromatography (2:1 of EtOAc:Hex). $^1$H NMR (CDCl$_3$): δ 7.2-7.34 (m, 5H), 3.85 (t, 1H), 3.60-3.70 (m, 2H), 3.42 (m, 1H), 3.14 (m, 2H), 3.09 (d, 2H), 1.28 (s, 3H), 1.13 (s, 3H). Elemental analysis for C$_{14}$H$_{20}$N$_2$O$_2$ (6)—calculated: C 67.71, H 8.12, N 11.28%; observed: C 67.12, H 7.99, N 11.52%.

Synthesis of (5S)-5-(4-allyldimethylsilylbutoxyl-benzyl)-2,2-dimethyl-3-(2-hydroxylethyl) imidazolidin-4-one (7). NaH (60% in oil, 480 mg, 12 mmol) was added to a DMF solution of 6 (2.47 g, 10 mmol) at 0° C. The resulting mixture was stirred for 3 h, and the ice bath was gradually warmed to room temperature. Allylbromobutyldimethylsilane (11 mmol) was then added. The resulting solution was stirred for another 5 h, and concentrated in vacuo at 65° C. to remove DMF. The residue was extracted with ether to remove the salts. Compound 7 was obtained as a colorless oil in 52% yield (2.09 g, 5.2 mmol) after silica gel chromatography (1:1 of EtOAc:Hex). $^1$H NMR (CDCl$_3$): δ 7.20-7.35 (m, 5H), 5.80 (m, 1H), 4.85 (m, 2H), 3.80 (t, 1H), 3.38-3.55 (m, 5H), 3.10-3.22 (m, 3H), 1.52 (m, 4H), 1.32 (m, 2H), 1.29 (s, 3H), 1.19 (s, 3H), 0.53 (m, 2H), 0.00 (s, 6H). Elemental analysis for C$_{23}$H$_{38}$N$_2$O$_2$Si (7)—calculated: C 68.61, H 9.51, N 6.96%; observed: C 68.22, H 9.00, N 7.23%.

Synthesis of (S)—(C$_2$H$_5$O)$_3$Si(CH$_2$)$_3$NHCONHCH(CH(CH$_3$)$_2$)CH$_2$OH (8D'). (S)-2-amino-3-methyl-1-butanol (676 mg, 5 mmol) was added to a dichloromethane solution of (C$_2$H$_5$O)$_3$Si(CH$_2$)$_3$NCO (1.24 g, 5 mmol). The resulting mixture was stirred for 3 days at room temperature, and concentrated in vacuo. Compound 8D' was obtained as a colorless oil in 82% yield (1.43 g, 4.1 mmol) after silica gel chromatography (1:1 of EtOAc:Hex). $^1$H NMR (CDCl$_3$): δ 5.77 (t, 1H), 5.66 (d, 1H), 4.65 (s, 1H), 3.95 (q, 6H), 3.80-3.90 (m, 3H), 3.43 (m, 2H), 2.04 (m, 1H), 1.90 (m, 2H), 1.34 (t, 9H), 1.11 (d, 6H), 0.85 (m, 2H). Elemental analysis for C$_{15}$H$_{34}$N$_2$O$_2$Si (8D')—calculated: C 51.40, H 9.78, N 7.99%; observed: C 51.11, H 9.43, N 8.22%.

Silane functionalization of MCF. Generally, deallylation reaction between allylsilane and alcohol or silanol needs to be catalyzed by acid, Without an acid catalyst, significant reaction can be achieved only with silica samples with acidic surface, such as FSM-16. By adding 2-5% acid catalyst, high silane loading could be achieved with all types of silica, even when the reaction was run at room temperature (see Table 4).

Table 4 shows that with the same reaction conditions, less silane loading was obtained with amorphous silica, compared to FSM-16 (synthesized at basic condition). MCF (synthesized at highly acidic condition) showed negligible silane loading when an acid was not added. With p-TsOH as a catalyst, a silane loading as high as 0.90 mmol/g and a greater silane coverage were achieved with MCF. Even when its surface silanols were pre-capped with 0.67 mmol TMS/g of MCF, an additional silane loading of 0.37 mmol/g was attained for MCF through the allylsilane reaction. The maximum TMS loading on MCF was ~1.1-1.2 mmol/g. When the reaction was performed at room temperature for 30 h, a high silane loading of 0.75 mmol/g was obtained on MCF. The silane loadings were determined by elemental analysis for chlorine.

Pre-capping of MCF with hexamethyldisilazane (HMDS). As-prepared MCF was dried under vacuum at 180° C. for 16 h. Dry toluene (30 mL) and HMDS (293 mg, 1.8 mmol) were added to the dried MCF (5 g), and the suspension was stirred at 60° C. for 16 h. The mixture was filtered, and the solid was washed with methanol, acetone and dichloromethane several times. After drying in vacuum, the MCF partially pre-capped with TMS (5.26 g) was collected and characterized. The IR spectrum shows a significant reduction in the silanol peak at 3730 cm$^{-1}$, and a strong C—H peak at 2960 cm$^{-1}$. The TMS loading was 0.67 mmol/g of MCF based on elemental analysis (C 2.41, H 0.77%), which was also in agreement with the weight gain after the reaction.

Immobilization of catalysts. As-prepared MCF (5 g) was dried overnight under vacuum at 180° C. Toluene (30 mL), catalyst precursor 4 (972 mg, 2.5 mmol) and p-TsOH (8.5 mg, 0.05 mmol) were added to the dried MCF sequentially. The suspension was stirred at 100° C. for 24 h, and filtered. The solid obtained was washed successively with methanol, acetone and dichloromethane. After drying in vacuum, catalyst 8A (5.57 g) was collected and characterized. Catalyst 8C was prepared in a similar manner except that a partially pre-capped MCF was used; this silica support was first dried overnight under vacuum at 85° C.

The IR spectrum for the catalyst-loaded MCF showed a significantly reduced silanol peak at 3730 cm$^{-1}$, and strong peaks associated with C—H and C═O at 2830-2970 cm$^{-1}$ and 1600-1700 cm$^{-1}$, respectively. The loading of 4 was 0.37 mmol/g of 8A, based on elemental analysis (C 7.78, H 1.26, N 1.02%) and weight gain. Elemental analysis—observed for 8C (0.67 mmol TMS/g and 0.14 mmol 4/g): C 6.01, H 1.06, N 0.39%; observed for 9C (0.67 mmol TMS/g and 0.12 mmol 5/g): C 4.59, H 0.85, N 0.34%; observed for 10C (0.67 mmol TMS/g and 0.11 mmol 7/g): C 5.57, H 1.23, N 0.30%.

Post-capping of catalyst-loaded MCF. MCF immobilized with catalyst (8A, 5.0 g) was dried under vacuum at 85° C. for 16 h. Dry toluene (30 mL) and HMDS (325 mg, 2 mmol) were then added to it, and stirred at 60° C. for 16 h. The mixture was filtered, and the solid was washed successively with methanol, acetone and dichforomethane. After drying in vacuum, the TMS-capped MCF immobilized with catalyst (8B, 5.52 g) was collected and characterized. The loadings of TMS and 4 were 0.8 mmol/g and 0.29 mmol/g, respectively, based on elemental analysis (C 9.61, H 1.81, N 0.63%) and weight gain.

Immobilization of catalyst with chiral modification. As-prepared MCF (5 g) was dried under vacuum at 180° C. for 16 h. Dry toluene (30 ml) and chiral modifier 8D' (1.75 g, 5 mmol) were added to the dried MCF. The suspension was stirred in toluene under reflux for 16 h. The mixture was filtered, and the solid was washed successively with methanol, acetone and dichloromethane. After drying in vacuum, the MCF modified with chiral molecules (CM) (5.98 g) was collected and characterized by IR and elemental analysis (C 10.27, H 1.80, N 2.29%). The loading of chiral molecules was 0.8 mmol/g based on elemental analysis and weight gain. The 8D'-modified MCF (5.98 g) was dried overnight under vacuum at 85° C. Then, toluene (30 mL), 4 (972 mg, 2.5 mmol) and p-TsOH (8.5 mg, 0.05 mmol) were added to it sequentially. The suspension was stirred at 100° C. for 24 h. The mixture was then filtered, and the solid was washed with methanol, acetone and dichloromethane several times. After drying in vacuum, catalyst 8D (6.22 g) was collected and characterized by IR and elemental analysis (C 14.71, H 2.53, N 2.86%). The loading of 4 is 0.2 mmol/g based on elemental analysis and weight gain.

was centrifuged, and the solution was decanted. This procedure was repeated at least three times using THF as the washing solvent. The recovered catalyst was used directly for the next run. The combined solution was prepared following literature procedure (N. A. Paras, D. W. C. MaxMillan, J. Am. Chem. Soc. 2001, 123, 4370) to give a pure alcoholic product in 72% yield (108 mg, 0.5 mmol). The 1H NMR data were in agreement with those reported. Enantioselectivity was determined by GLC analysis of the corresponding aldehyde (Chiraldex □-TA column, 0.25 mm×30 m, 5° C./min ramp from 70° C. to 170° C., 23 psi); R isomer: tr=26.6 min, and S isomer: tr=27.4 min.

Diels-Alder reaction (Table 3, Entry 2). MCF-supported catalyst 8C (0.5 g, 0.07 mmol) was treated with acetonitrile (15 mL), $H_2O$ (0.75 mL) and aqueous TFA solution (0.5 M, 140 μL, 0.07 mmol). The mixture was stirred for 10 min, and then trans-cinnamaldehyde (177 μL, 1.4 mmol) was added. After 5 min, cyclopentadiene (1.68 mmol) was added. The suspension was stirred at room temperature, and the reaction was monitored by TLC. The resulting suspension was centrifuged, and the solution was decanted. This procedure was repeated at least three times by using MeCN as the washing solvent. The recovered catalyst was used directly for the next run. The combined solution was prepared following literature procedure (K. A. Ahrendt, C. J. Borths, D. W. C. MaxMillan, J. Am. Chem. Soc. 2000, 122, 4243) to give a pure product in 93% yield (264 mg, 1.31 mmol). The $^1H$ NMR data obtained for the product agreed with those reported in the literature (K. Ishihara, H. Kurihara, M. Matsumoto, H. Yamamoto, J. Am. Chem. Soc. 1998, 120, 6920). The exo:endo ratio was obtained from $^1H$ NMR results. Enantioselectivity was determined by GLC analysis of the corresponding aldehyde (Chiraldex β-PH column, 0.25 mm×30 m, 1.5° C./min ramp from 60° C. to 170° C., 23 psi); endo isomers: $t_r$=53.2 min and 53.5 min, exo isomers: $t_r$=52.2 min and 52.8 min.

TABLE 4

Reaction of allylchloropropyldimethylsilane with silica surface in toluene.

| Allylsilane (mmol/g) | p-TsOH (mmol/g) | Silica Support | Surface Area ($m^2/g$) | Temperature (° C.) | Time (h) | Silane Loading (mmol/g) | Silane Coverage[a] (%) |
|---|---|---|---|---|---|---|---|
| 3 | — | FSM-16 | 966 | 120 | 15 | 1.1[5] | 22 |
| 10 | — | FSM-16 | 966 | 120 | 15 | 1.6[5] | 32 |
| 10 | — | Silica[b] | 480 | 120 | 15 | 0.3[5] | |
| 3 | — | MCF | 504 | 120 | 15 | 0.056 | 2.8 |
| 5 | — | MCF/HCl | 504 | 120 | 15 | 0.40 | 20 |
| 5 | 0.10 | MCF | 504 | 120 | 15 | 0.90 | 45 |
| 1.5[c] | 0.03 | MCF | 504 | 120 | 15 | 0.64 | 32 |
| 1.5 | 0.06 | MCF[d] | 504 | 120 | 15 | 0.37 | 52 |
| 2 | 0.12 | MCF | 504 | 50 | 15 | 0.72 | 36 |
| 5 | 0.10 | MCF | 504 | 25 | 30 | 0.75 | 37.5 |
| 2[e] | 0.12 | MCF | 504 | 25 | 15 | 0.42 | 21 |
| 2[e] | 0.03 | MCF | 504 | 25 | 15 | 0.28 | 14 |

[a]Silane loading/total silanol. 100% coverage corresponded to 5 mmol/g for FSM-16 and ~2 mmol/g for MCF.
[b]Amorphous silica.
[c]Allylbromophenyldimethylsilane was used instead of allylchloropropyldimethylsilane.
[d]pre-capped by 0.67 mmol of TMS/g of MCF.
[e]MeCN was used as solvent instead of toluene.

Friedel-Crafts alkylation (Table 1, Entry 10). MCF-supported catalyst 8C (0.5 g, 0.07 mmol) was treated with THF (8 ml), $H_2O$ (0.5 mL) and aqueous TFA solution (0.5 M, 140 μL, 0.07 mmol). The mixture was stirred for 10 min, and then N-methylpyrrole (310 μL, 3.5 mmol) was added. Next, trans-cinnamaldehyde (88 μL, 0.7 mmol) was dripped into the reaction vial. The suspension was stirred at room temperature, and the reaction was monitored by TLC. The suspension

The invention claimed is:

1. A heterogeneous catalyst comprising an organic catalytic group coupled to a mesocellular siliceous foam support, said catalyst additionally having alkylsilyl groups or one or more chiral modifiers or both and said chiral modifier(s) being different to the catalytic group, wherein the catalytic group is capable of catalysing a reaction selected from the group consisting of a Friedel-Craft reaction and a Diels-Alder reaction and wherein the catalytic group is coupled to the support by a linker group comprising an attachment group for attaching the linker group to the support and a spacer group which couples the attachment group to the catalytic group, wherein the spacer group is selected from the group consisting of —($CH_2$)$_4$—O—$C_6H_4$—$CH_2$— and —($CH_2$)$_2$—O—($CH_2$)$_4$—, and wherein the catalyst is made by coupling a reagent comprising the organic catalytic group and the linker group to silanols on the mesocellular siliceous foam support, said support having the alkylsilyl groups or one or more chiral modifiers or both coupled thereto prior to said coupling of said reagent to said silanols.

2. The heterogeneous catalyst of claim 1 wherein the catalytic group is capable of catalyzing the reaction to produce a chiral product.

3. The heterogeneous catalyst of claim 1 wherein the catalytic group is chiral.

4. The heterogeneous catalyst of claim 1 wherein the catalytic group has either greater than 75% (+) chirality or greater than 75% (−) chirality.

5. The heterogeneous catalyst of claim 1 wherein the catalytic group comprises an imidazolidin-4-one group.

6. The heterogeneous catalyst of claim 5 wherein the imidazolidin-4-one group is substituted on C5.

7. The heterogeneous catalyst of claim 5 wherein the imidazolidin-4-one group is substituted on C5 by an arylmethyl group.

8. The heterogeneous catalyst of claim 5 wherein the imidazolidin-4-one group is coupled to the support through either N3 or C5 of the imidazolidin-4-one.

9. The heterogeneous catalyst of claim 1 wherein the alkylsilyl groups are trimethylsilyl groups.

10. The heterogeneous catalyst of claim 1 wherein the attachment group comprises —$SiMe_2$-.

11. The heterogeneous catalyst of claim 1 comprising a 3-alkylimidazolidin-4-one group coupled through C5 to a mesocellular siliceous foam support by —$CH_2$—$C_6H_4$—O—($CH_2$)$_4$—Si($Me_2$)-, and also comprising trimethylsilyl groups coupled to the support.

12. The heterogeneous catalyst of claim 1 comprising a 5-(phenylmethyl)imidazolidin-4-one group coupled through N3 to a mesocellular siliceous foam support by —($CH_2$)$_2$—O—($CH_2$)$_4$—Si($Me_2$)-, and also comprising trimethylsilyl groups coupled to the support.

13. The heterogeneous catalyst of claim 1 wherein the one or more chiral modifiers comprise an amine bearing a chiral group.

14. The heterogeneous catalyst of claim 1,
wherein the heterogeneous catalyst is capable of catalyzing an asymmetric Friedel-Craft alkylation to produce a chiral product with an enatioselectivity from about 68% ee to about 100% ee.

15. The heterogeneous catalyst of claim 14, wherein the enatioselectivity is from about 70% ee to about 100% ee.

16. The heterogeneous catalyst of claim 15, wherein the enatioselectivity is from about 74% ee to about 100% ee.

17. The heterogeneous catalyst of claim 16, wherein the enatioselectivity is from about 92% ee to about 100% ee.

18. The heterogeneous catalyst of claim 1, wherein said coupling is a one-step process.

* * * * *